US008648203B2

(12) United States Patent
Cohen et al.

(10) Patent No.: US 8,648,203 B2
(45) Date of Patent: Feb. 11, 2014

(54) PROCESS FOR PREPARING PYRIDINAMINES AND NOVEL POLYMORPHS THEREOF

(75) Inventors: Shlomi Cohen, Beer Sheva (IL); Sharona Zamir, Omer (IL)

(73) Assignee: Makhteshim Chemical Works Ltd., Beer Sheva (IL)

( * ) Notice: Subject to any disclaimer, the term of this patent is extended or adjusted under 35 U.S.C. 154(b) by 0 days.

(21) Appl. No.: 13/444,833

(22) Filed: Apr. 11, 2012

(65) Prior Publication Data

US 2012/0197023 A1    Aug. 2, 2012

Related U.S. Application Data

(62) Division of application No. 12/094,879, filed as application No. PCT/IL2006/001351 on Nov. 23, 2006, now Pat. No. 8,163,930.

(30) Foreign Application Priority Data

Nov. 23, 2005  (IL) .......................................... 172137
Dec. 19, 2005  (IL) .......................................... 172685

(51) Int. Cl.
*A61K 31/44*     (2006.01)
*C07D 213/72*    (2006.01)

(52) U.S. Cl.
USPC .......................................... 546/304; 514/357

(58) Field of Classification Search
None
See application file for complete search history.

(56) References Cited

U.S. PATENT DOCUMENTS

| 3,926,611 A | 12/1975 | Tomlin et al. | |
| 3,965,109 A | 6/1976 | Tomlin et al. | |
| 4,140,778 A | 2/1979 | Dreikorn | |
| 4,331,670 A * | 5/1982 | Nishiyama et al. | 514/352 |
| 5,081,133 A * | 1/1992 | Schubert et al. | 514/344 |
| 2007/0081947 A1 | 4/2007 | Eble et al. | |

FOREIGN PATENT DOCUMENTS

| JP | 60-123471 | 7/1985 |
| WO | 2009017239 | 2/2009 |
| WO | 2009017241 | 2/2009 |
| WO | 2009054210 | 4/2009 |
| WO | 2011/092618 | 8/2011 |
| WO | 2011092618 | 8/2011 |

OTHER PUBLICATIONS

Office Action issued Feb. 17, 2010, by the New Zealand Patent Office in Appln No. 567671, 3 pages.
Reynolds v Herbert Smith & Co., Ltd, decision of Nov. 27, and 28, 1902, pp. 123-128.
British Celanese Ltd v Courtaulds Ltd. decision of Oct. and Nov. 1934 and Feb. 11, 1935, pp. 171-200.
L & G's Patent Application decision of Nov. 20 and Dec. 3, 1940, pp. 21-24.
Sabaf SPA v MFI Furniture Centres Ltd. decision of Oct. 14, 2004, pp. 209-219.
Nakajima et al, "Synthesis and Fungicidal Activity of N-Phenylpridinamines," ACS Symposium Series 1995, pp. 443-448.
Soji Awatsu et al, "New Preparations," published by Nazando on Nov. 25, 1982, pp. 1-5 ("1. Crystals of medicines" to "2. polymorphism").
Manufacture Technology of Solid Tablet, published by CMC Publishing Co., Ltd. Jan. 27, 2003, pp. 1-6.
"Pesticide Manual" 2003 edition, pp. 446-447.
Publication of court decision, Action No. Heisei 18 (gyo-ke) No. 10271, pp. 1-50, Oct. 26, 2007.
Naki and Hanano, "New Drug Formulation," publisher: Shoji Suzuki: published by Nanzando Co., Ltd., published Nov. 25, 1982 (D1, 2 pages).
Shioji, "Manufacture technology of Solid Tablet," Mar. 5, 185 (D2, 3 pages).
Translation of the bibliographic particulars of IP Court Decision [Case Hei=18 (Gyou-ke) 10271] (D6, 1 page) Mar. 31, 2011.
Translation of the relevant portions of IP Court Decision in Case Hei-18 (Gyou-ke) 1027 (D6, 1 page) Mar. 31, 2011.
Third party observations filed in Japan on Mar. 31, 2011, against the corresponding application JP 2008-541911, pp. 1-13.
English text of the First Official Action in China for Appln No. 200680043978.X (Mar. 31, 2011), 5 pages.
Cabri, et al., Polymorphisms and Patent, Market, and Legal Battles: Cefdinir Case Study, Organic Process Research & Developemnt, 2007, pp. 64-72, vol. 11.
Caira, Mino R., Crystalline Polymorphism of Organic Compounds, Topics in Current Chemistry, 1998, pp. 163-208, vol. 198.
International Preliminary Report on Patentability for International Appl. No. PCT/IL2006/001351, Date of issuance of report Jan. 13, 2009.
Dr. Sofia Papathoma, Patenting Polymorphs at the European Patent Office, Presentation in Barcelona Jun. 19-21, 2006, pp. 1-28.
Supplementary European Search Report for EP Appl. No. 06 82 1571, mail date Aug. 3, 2010.
Third Party Observation in the European Patent Office on Jul. 18, 2008 in EP Appl. No. 06821571.4-1216.

(Continued)

*Primary Examiner* — Janet L Andres
*Assistant Examiner* — Heidi Reese
(74) *Attorney, Agent, or Firm* — Browdy and Neimark, PLLC

(57) ABSTRACT

The present invention relates to an improved process for the synthesis and purification of 3-chloro-N-(3-chloro-5-tri-fluoromethyl-2-pyridyl)-α,α,α-trifluoro-2,6-di-nitro-p-toluidine (fluazinam) and other pyridinamines, which implements methyl isobutyl ketone (MIBK) as the reaction solvent. The process of the invention overcomes the drawbacks of prior art methods, by reducing the side reactions such as hydrolysis, eliminating the need for difficult and labor-intensive purification methods, and providing pure products in higher yields. The present invention relates to novel crystalline polymorphic forms fluazinam, and to mixtures of the polymorphs. The present invention also provides methods for preparing the novel polymorphs, as well as pharmaceutical compositions comprising same, and methods of using the polymorphs as pesticidal agents for combating noxious living organisms on agricultural and horticultural crops.

25 Claims, 9 Drawing Sheets

(56) References Cited

OTHER PUBLICATIONS

Third Party Observation in the European Patent Office on Nov. 21, 2012 in Ep Appl. No. 06821571.4-2117.

Soji Awatsu et al, New Preparations, published by Nazando on Nov. 25, 1982, pp. 1-5 ("1. Crystals of medicines" to "2. polymorphism").
Shioji, Manufacture technology of Solid Tablet, Mar. 5, 1985 (D2, 3 pages).

* cited by examiner

PROCESS FOR PREPARING PYRIDINAMINES AND NOVEL POLYMORPHS THEREOF

This is a divisional of allowed application Ser. No. 12/094,879, filed Nov. 12, 2008, now U.S. Pat. No. 8,163,930, such application being the U.S. National Phase of International Application No. PCT/IL06/001351, Nov. 23, 2006, the entire contents of each of which are incorporated herein by reference.

FIELD OF THE INVENTION

The present invention relates to the synthesis of pyridinamines, and more specifically to an improved method for the synthesis of N-phenylpyridinamines such as 3-chloro-N-(3-chloro-5-trifluoromethyl-2-pyridyl)-α,α,α-trifluoro-2,6-dinitro-p-toluidine (fluazinam), a pesticidal agent. The present invention relates to novel crystalline polymorphs of fluazinam, to processes for their preparation, compositions comprising the polymorphs and their use as pesticidal agents.

BACKGROUND OF THE INVENTION

Certain pyridinamines have pesticidal activities for combating noxious living beings such as insects, mites, fungi, bacteria and rodents. For example, compounds having rodenticidal activity are disclosed in U.S. Pat. No. 4,140,778 and compounds having pesticidal activity are disclosed in U.S. Pat. No. 3,965,109 and U.S. Pat. No. 3,926,611.

U.S. Pat. No. 4,331,670 discloses and claims N-pyridinamines having specific substituents on the pyridyl ring. These compounds are effective at combating noxious insects, mites, fungi, and bacteria on industrial products, seeds and fruits in storage, and for controlling noxious organisms growing on agricultural and horticultural crops and up-land. One of these compounds, fluazinam, is currently marketed for managing *sclerotinia* drop which is a major disease of lettuce caused by two soil borne fungi: *S. minor* and *S. sclerotiorum*. Fluazinam and other fungicides such as boscalid, fenhexamid, and fludioxonil have also demonstrated efficacy against diseases caused by *S. minor* and *S. sclerotiorum* on crops other than lettuce.

3-chloro-N-(3-chloro-5-trifluoromethyl-2-pyridyl)-α,α,α-trifluoro-2,6-dinitro-p-toluidine (fluazinam), is also known to assist in the protection of container-grown aucuba from southern blight, a damaging hot weather disease afflicting a wide variety of flowering trees, shrubs and herbaceous ornamentals in both the nursery and landscape.

Fluazinam has a broad antifungal spectrum and shows good preventive effect against plant diseases. Fluazinam showed good activity against benzimidazole and/or dicarboximide resistant strains of *B. cinerea*. Field tests demonstrated excellent activity of fluazinam against potato Phycophthora infestans. Fluazinam was also shown to significantly reduce the population of mites by repeated treatments in the field. (*ACS Symposium Series* 1995 584, 443-8).

U.S. Pat. No. 4,331,670, the contents of which are incorporated by reference herein in their entirety, discloses a coupling process for the preparation of pyridinamines such as fluazinam according to the following scheme:

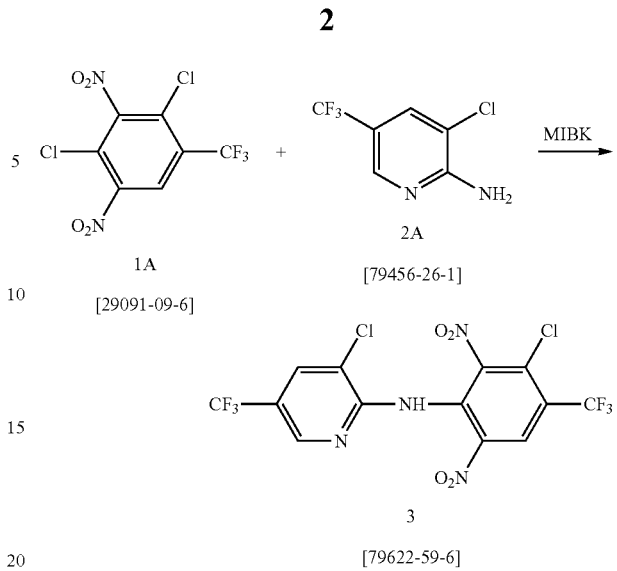

The reaction utilizes either THF or DMF as solvent, leading to a reported yield of 75% and 22%, respectively. The aforementioned solvents cause the reaction to suffer from many drawbacks. For example, THF is a flammable unsafe solvent with a low flash point and is a source for peroxide formation; hence its use in large-scale production is very limited. In addition, aprotic polar solvents such as THF and DMF are water-miscible and recycle as azeotropes containing high amounts of water. The presence of water lowers the yield of the reaction due to incomplete consumption of the reagents on one hand and the manufacture of hydrolysis byproducts on the other. For example, a competing side-reaction is the hydrolysis of compound (1A) in the presence of water to generate the resulting by-product of formula (4). This reaction significantly lowers the yield of the final product.

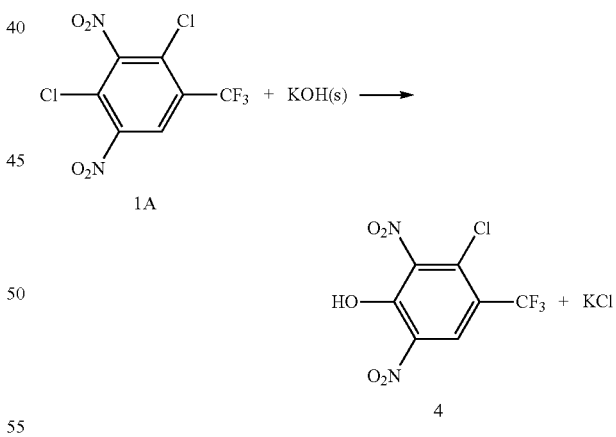

In addition, the prior art method involves very tedious work-up steps that involve extraction into a third solvent—ethyl acetate and purification on silica gel, which is unsuitable for large-scale manufacture. These complicated purification procedures are needed in order to remove the large amounts of impurities formed during the reaction such as the hydrolysis products described above, as well as accelerated tar formation at temperatures above 40° C., and incomplete consumption of both reagent 1A and 2A (mainly due to the dilute conditions under which the reaction is conducted—less then 8.2% w/v reagents to solvent).

To date, there are no simple methods for purifying fluazinam, which can be used on a large scale to produce highly pure product. There are also no known crystalline polymorphic forms of fluazinam. There is thus an urgent and unmet need in the art for efficient methods for the preparation and purification of fluazinam and other pyridinamines, which overcome the drawbacks and deficiencies of the prior art methods.

SUMMARY OF THE INVENTION

The present invention relates to an improved process for the synthesis of 3-chloro-N-(3-chloro-5-trifluoromethyl-2-pyridyl)-α,α,α-trifluoro-2,6-dinitro-p-toluidine (fluazinam) and other pyridinamines, which implements methyl isobutyl ketone (MIBK) as the reaction solvent. The process of the invention overcomes the drawbacks of prior art methods, by reducing side reactions such as hydrolysis, eliminating the need for difficult and labor-intensive purification methods, and providing pure products in higher yields. In another aspect, the present invention relates to novel crystalline polymorphic forms of fluazinam, and to mixtures of these polymorphs. The present invention also provides methods for preparing the novel polymorphs, as well as pesticidal compositions comprising same, and methods of using the polymorphs as pesticidal agents for combating noxious living beings on agricultural and horticultural crops.

As contemplated herein, the applicants of the present invention have unexpectedly found that the use of MIBK as a reaction solvent for preparing fluazinam and other pyridinamines provides a more efficient process which is less labor-intensive and which dramatically improves both the yield and purity of the pyridinamine product. This presents a significant improvement over prior art methods which utilize THF or DMF as solvents. First, the chemical yield improves from 22% when DMF is used and 75% when THF is used, to about 98%. In addition, the methods of the invention allow for easy work-up procedures, by replacing the tedious column purification by simple crystallization procedures.

Without wishing to be bound by any particular mechanism or theory, it is believed that these advantages are the result of several beneficial properties of MIBK, including: 1) easy recycling and improved safety; 2) low water content of the recycled solvent (1.6%) compared to that of THF (5%); 3) low water solubility and 4) reduced sensitivity to temperature fluctuation. The low water solubility of MIBK minimizes the amount of water present during the reaction, thereby decreasing the amount of hydrolysis by-products and increasing the yield. The reduced sensitivity to temperature fluctuation is important, particularly since the reaction is very exothermic and at high temperature, large amounts of tar are produced.

Furthermore, a drawback of the prior art methods is the incomplete consumption of both reactants (1A) and (2A), due mainly to the dilute conditions under which the reaction is conducted (less than 8.2 weight/volume (w/v) reagents to solvent). Specifically, when solvents such as THF, DMF and other water-miscible solvents are used, the reaction cannot be conducted under concentrated conditions, since the high concentration of water produced in the reaction and present in the reagents themselves will increase the amount of hydrolysis by-products, thus lowering the yield. This phenomenon is not observed when MIBK is used, due mainly to its low water solubility. In fact, the applicants have unexpectedly discovered that the more concentrated the reaction, the less that hydrolysis is observed. The use of MIBK thus permits the reaction to be conducted under more concentrated conditions, significantly increasing the efficiency of the reaction.

As used herein, the term "reagents to solvent ratio" means the total weight of reagents of formulas A and B (or formulas 1 and 2 or formulas 1A and 2A) per volume of the solvent in the reaction mixture as expressed as percentage ratio of weight per volume (w/v). In one embodiment the reagents to solvent ratio is at least about 10%. Preferably, the reagents to solvent ratio is at least about 25%, more preferably at least about 40% weight/volume (w/v).

It is therefore an object of present invention to provide a novel process for preparing pryridinamine compounds represented by the structural formula (I)

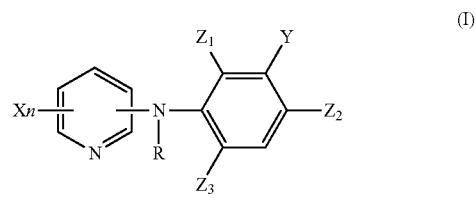

wherein X is a trifluoromethyl group, a halogen atom, a $C_1$-$C_6$ alkyl group or a $C_1$-$C_6$ alkoxy group; n is an integer of 0 to 4; R is a hydrogen atom or an acetyl group; Y a hydrogen atom, a halogen atom, a $C_1$-$C_6$ alkoxy group, $C_1$-$C_6$ thioalkyl group, an alkylthio group, a hydroxy group, an azido group, a phenoxy group or a phenoxy group in which the phenyl is substituted with a hydroxy; and $Z_1$, $Z_2$ and $Z_3$ are independently a trifluoromethyl group or a nitro group.

According to the process of the invention, these pyridinamines are synthesized by reacting a compound of formula (A) with a compound of formula (B), wherein X, Y, $Z_1$, $Z_2$, $Z_3$ and n in the formulas (A) and (B) are defined above and one of U and W is amino and the other is a leaving group, e.g., halogen, alkylsulfonyl, arylsulfonyl in the presence of a base, wherein MIBK is used as the reaction solvent.

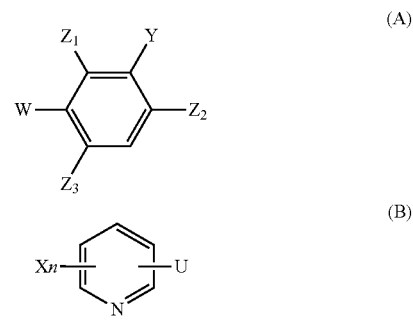

In one embodiment, MIBK is used as a pure solvent. The term "pure solvent" as used herein refers to at least about 98% purity. In another embodiment, MIBK is at least about 99% pure. In yet another embodiment, MIBK is at least about 99.5% pure. In yet another embodiment, MIBK is at least about 99.8% pure. In another embodiment, recycled MIBK containing less than about 2% of water is used. In a currently preferred embodiment, a recycled azeotrope of MIBK containing 1.6% of water is used.

In another embodiment, the present invention provides a process for the preparation of the pyridinamine known as fluazinam, represented by formula (3), by reacting compound of formula (1) with a compound of formula (2), wherein one of U and W is amino and the other is a leaving group selected from the group consisting of halogen, alkylsulfonyl and arylsulfonyl, in the presence of a base, using MIBK as a reaction solvent.

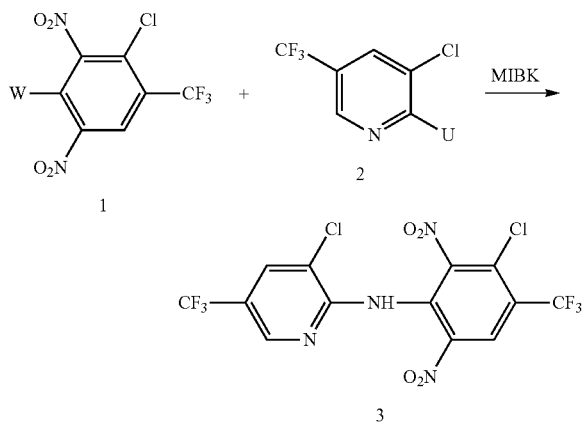

The process is conducted in a base, preferably selected from a group consisting of alkali metal hydroxides, alkali metal carbonates, hydrides, alkaline earth metal hydroxides and alkaline earth metal carbonates.

In a currently preferred embodiment, the base is potassium hydroxide or sodium hydroxide.

In another embodiment, the present invention, provides a process for the preparation of fluazinam, represented by formula (3), by reacting compound of formula (1A) with a compound of formula (2A), using MIBK as a reaction solvent.

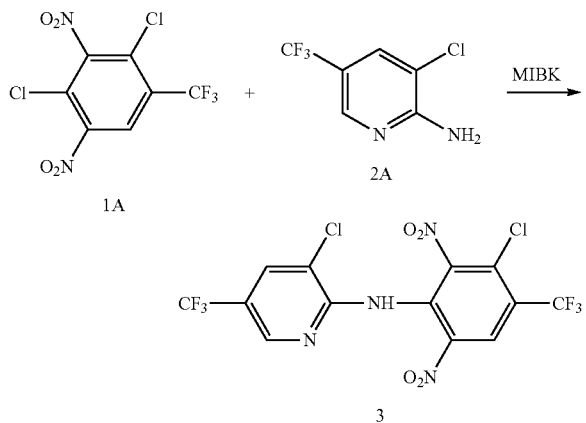

The process is conducted in a base, preferably selected from a group consisting of alkali metal hydroxides, alkali metal carbonates, hydrides, alkaline earth metal hydroxides and alkaline earth metal carbonates.

In a currently preferred embodiment, the base is potassium hydroxide or sodium hydroxide.

It is another object of the present invention to provide a process for purifying a compound of formula (I) comprising the step of crystallizing said compound from a solvent or mixture of solvents. An organic solvent or mixtures of organic solvents are preferred for the crystallization. A currently preferred organic solvent in the crystallization step is ethanol.

It is yet another object of the present invention to provide a process for purifying fluazinam comprising the step of crystallizing said compound from a solvent or a mixture of solvents. A currently preferred solvent is ethanol. As contemplated herein, the crystallization methods described herein may lead to the formation of novel polymorphic forms of fluazinam, or mixtures thereof. These polymorphic forms or mixtures thereof also form part of this invention.

Thus, in another aspect, the present invention provides novel polymorphic forms of fluazinam, and processes for their preparation. In one embodiment, the present invention provides a novel crystalline polymorphic form of fluazinam, designated "Form I". Form I exhibits an X-ray powder diffraction pattern substantially as shown in FIG. 1, having characteristic peaks (expressed in degrees 2θ (+/−0.2°θ) at one or more of the following positions: 8.7, 10, 12.0, 13.7, 14.5, 17.4, 18.5, 19.7, 21.8, 22.9, and 30.2. Form I also exhibits an infrared (IR) spectrum at the 3000 cm$^{-1}$ range substantially as shown in FIG. 2, having a characteristic peak at about 3390 cm$^{-1}$. Form I also exhibits a Differential Scanning calorimetry (DSC) thermogram substantially as shown in FIG. 3, which is characterized by a predominant endotherm peak at about 115.5° C. as measured by Differential Scanning calorimeter at a scan rate of 10° C. per minute. Form I generally crystallizes in the form of prisms, typically as large yellow prisms, as described herein.

In another embodiment, the present invention provides a novel crystalline polymorphic form of fluazinam designated "Form II". Form II exhibits an X-ray powder diffraction pattern substantially as shown in FIG. 4, having characteristic peaks (expressed in degrees 2θ (+/−0.2°θ) at one or more of the following positions: 7.4, 10.4, 13.4, 15.1, 18.95, 20, 20.4, 21.05, 21.3, 22.2, 24.9, 27.15, 28.6, and 30.5. Form II also exhibits an IR spectrum at the 3000 cm$^{-1}$ range substantially as shown in FIG. 5, having a characteristic peak at about 3375 cm$^{-1}$. Form II also exhibits a DSC thermogram substantially as shown in FIG. 6, which is characterized by a predominant endotherm at about 109° C., as measured by Differential Scanning Calorimeter at a scan rate of 10° C. per minute. Form H generally crystallizes in the form of needles, typically as bright yellow needles.

In yet another embodiment, the present invention provides a mixture of polymorphic Form I and Form II of fluazinam. The mixture exhibits an X-ray powder diffraction pattern substantially as shown in FIG. 7, an IR spectrum at the 3000 cm$^{-1}$ range substantially as shown in FIG. 8, and a DSC thermogram substantially as shown in FIG. 9, as measured by Differential Scanning Calorimeter at a scan rate of 10° C. per minute.

In another aspect, the present invention provides processes for preparing the novel polymorphs of fluazinam Form I and Form II, as well as processes for producing mixtures of the polymorphs.

In one embodiment, Form I fluazinam can be prepared by crystallizing fluazinam from a solvent selected from the group consisting of ethanol, acetonitrile, methylene chloride and n-hexane; and isolating the resulting crystals. In a currently preferred embodiment, the process includes preparing a solution of the compound is one or more of the aforementioned solvents, preferably by applying heat until dissolution is complete, cooling the solution until crystals appear, and isolating the crystals.

In another embodiment, Form I and Form II of fluazinam can be prepared by crystallizing fluazinam from diethyl ether, using different crystallization conditions. To prepare Form I, fluazinam is dissolved in diethyl ether, preferably at room temperature, and the flask is exposed to the environment so that the solvent slowly evaporates. Gradually, crystals begin to appear, typically in the form of large yellow prisms, which are then isolated. To prepare Form II, the compound is also dissolved in diethyl ether as described above, but the solvent is rapidly evaporated from the flask. This leads to the formation of crystals, typically in the form of bright yellow needles, which are then isolated.

In another embodiment, Form II can be prepared by preparing a solution of fluazinam in ethanol as described above with respect to Form I. However, instead of cooling to precipitate the product, the solution is left to stand exposed to the environment, so that part of the solvent slowly evaporates. Gradually, crystals begin to appear, typically in the form of bright yellow needles, which are then isolated.

In another embodiment, a mixture of Form I and Form II can be prepared by crystallizing fluazinam from a solvent selected from the group consisting of isopropyl alcohol, n-hexane and toluene; and isolating the resulting crystals. In a currently preferred embodiment, the process includes preparing a solution of fluazinam is one or more of the aforementioned solvents, preferably by applying heat until dissolution is complete, cooling the solution until crystals appear, and isolating the crystals.

The mixture of Form I and Form II can also be prepared by dissolving fluazinam in a solvent in which said compound is soluble, adding an anti-solvent, and isolating the resulting crystals. In one currently preferred embodiment, the solvent is acetone. In another currently preferred embodiment, the anti-solvent is water.

In another aspect, the present invention provides pesticidal compositions comprising the novel crystalline polymorphs, which are useful for controlling and combating noxious living organisms growing on agricultural and horticultural crops and up-land, for example insects, mites, fungus and bacteria. In one embodiment, the compositions comprise a crystalline polymorph Form I fluazinam; and an acceptable adjuvant. In another embodiment, the composition comprises a crystalline polymorph Form II of fluazinam; and an acceptable adjuvant. In yet another embodiment, the composition comprises a mixture of a crystalline polymorph Form I and II of fluazinam; and an acceptable adjuvant.

The present invention also relates to methods for combating insects, mites, fungus and bacteria, by contacting the insects, mites, fungus or bacteria with or exposing them to an effective amount of the compositions of the invention.

The present invention also relates to methods for protecting crops and upland, including industrial products thereof, such as seeds and fruits, by applying to the crops or products thereof an effective amount of the compositions of the invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
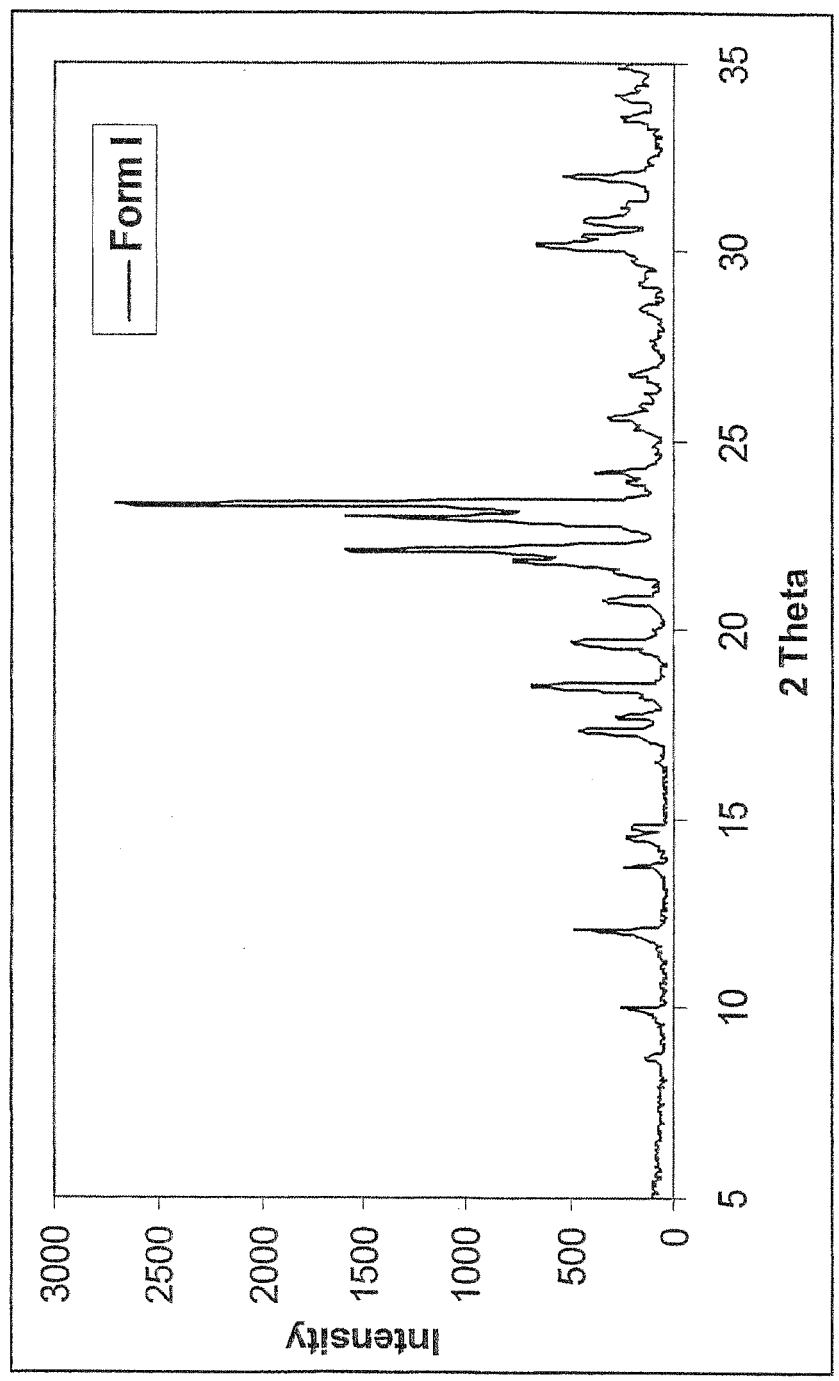
FIG. 1 is an X-ray powder diffraction spectrum of fluazinam Form I.

In one aspect, the present invention relates to an improved process for the synthesis of 3-chloro-N-(3-chloro-5-trifluoromethyl-2-pyridyl)-α,α,α-trifluoro-2,6-dinitro-p-toluidine (fluazinam) and other pyridinamines, which implements methyl isobutyl ketone (MIBK) as the reaction solvent. The process of the invention overcomes the drawbacks of prior art methods, by reducing side reactions such as hydrolysis, eliminating the need for difficult and labor-intensive purification methods, and providing pure products in higher yields.

Without wishing to be bound by any particular mechanism or theory, it is believed that, although water is needed for the work-up step of the reaction, particularly for product isolation by acidification, it has a negative role in the coupling reaction between compound A and compound B. Specifically, it is believed that water is responsible for the incomplete consumption of the reagents by producing hydrolysis by-products. Water is introduced from three different sources: 1) it is produced stoichiometrically by the neutralization of the emitted hydrochloric acid; 2) the solid inorganic base such as KOH and NaOH used in the reaction contain between 10-15% water; and 3) the use of water-miscible solvents such as THF, DMF and DMSO introduces water since the water-miscible solvents recycle as azeotropes with water.

In order to avoid these problems, the prior art reactions in THF or DMF have been conducted under very dilute conditions, so as to minimize the local concentration of water. However, this has led to a significant reduction in the yield and efficiency of the reaction.

As contemplated herein, the applicants screened several solvents having different water solubilities, as reaction solvents in a process for the synthesis of fluazinam and other pyridinamines according to the schemes shown above. Table 1 shows the physical data of several of the tested solvents.

TABLE 1

Physical data of some potential solvents

| Solvent | MW | b.p. (pure) | b.p. (Azeotrop) | % Solvent (Az.) | % Solvent (Top Layer) |
|---|---|---|---|---|---|
| MIBK | 100 | 115 | 88 | 76% | 98.40% |
| THF | 86 | 66 | 64 | 95% | None |
| ACN | 41 | 82 | 77 | 84% | None |
| MEK | 72 | 80 | 73 | 88% | None |
| DMF | 73 | 153 | None | 100% | |
| DMSO | 78 | 189 | None | 100% | |
| EtOH | 46 | 78 | 78 | 96% | None |

The applicants have surprisingly found that MIBK is a superior solvent for the coupling reactions. MIBK is distilled as a 76% solvent azeotrope. However, due to its low water solubility, two layers are formed upon standing, such that the organic rich layer contains about 98.4% MIBK and the aqueous rich layer contains about 1.6% MIBK. MIBK is the only solvent, from the ones studied, where the water content of its azeotrope (24%) differs significantly from the water content of its recycled solvent (1.6%).

Without wishing to be bound by any particular mechanism or theory, it is contemplated that the advantages of MIBK as a reaction solvent are, at least in part, due to its unique properties, including its low water solubility and low water content of the recycled solvent.

MIBK was found to be the optimal solvent that overcomes the problem of excess water formation, by allowing only to a minimum amount of "effective water" to interface with the reaction. The low water solubility of MIBK, which shields the reaction from excess water, enables to work in more concentrated systems. This is optimal for large-scale production improving both chemical and volume yield. Indeed, the chemical yield improves from 75% to 98%, and the volume yield (i.e. reagents to solvent ratio) improves from 8.2% to at least about 40% w/v.

Another advantage in using MIBK is that MIBK is known to be less sensitive than the other solvents to temperature fluctuations. This is important since the reaction is very exothermic and at high temperatures large amounts of tar are produced. The use of MIBK as the solvent also enables easy work up by replacing column purification by simple crystallization.

It is therefore an object of present invention to provide a novel process using a solvent that is effective in preparing pyridinamine compounds represented by the structural formula (I)

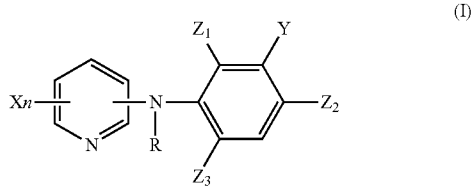

wherein X is a trifluoromethyl group, a halogen atom, a $C_1$-$C_6$ alkyl group or a $C_1$-$C_6$ alkoxy group; n is an integer of 0, 1, 2, 3 or 4; R is a hydrogen atom or an acetyl group; Y a hydrogen atom, a halogen atom, a $C_1$-$C_6$ alkoxy group, a $C_1$-$C_6$ thioalkyl group, a hydroxy group, an azido group, a phenoxy group or a phenoxy group in which the phenyl is substituted with a hydroxy; and $Z_1$, $Z_2$ and $Z_3$ are independently a trifluoromethyl group or a nitro group.

According to the process of the invention, these pyridinamines are synthesized by reacting a compound of formula (A) with a compound of formula (B), wherein X, Y, $Z_1$, $Z_2$, $Z_3$ and n in the formulas (A) and (B) are defined above and one of U and W is amino and the other is a leaving group selected from the group consisting of halogen, alkylsulfonyl, arylsulfonyl, in the presence of a base, wherein. MIBK is used as the reaction solvent. In one embodiment, MIBK is used as a pure solvent. In another embodiment, a recycled azeotrope of MIBK containing about 1.6% of water is used.

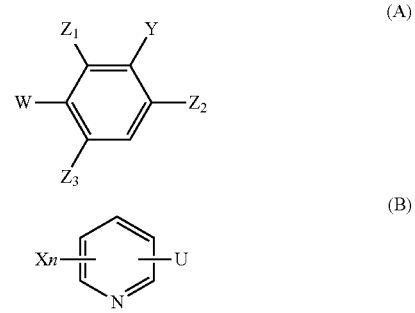

The term "$C_1$-$C_6$ alkyl" used herein alone or as part of another group denotes linear, branched or cyclic (e.g., cycloalkyl), saturated or unsaturated (e.g., alkenyl, alkynyl) groups, the latter only when the number of carbon atoms in the alkyl chain is greater than or equal to two, and can contain mixed structures. Examples of saturated alkyl groups include but are not limited to methyl, ethyl, n-propyl, isopropyl, n-butyl, iso-butyl, sec-butyl, tert-butyl, amyl, tert-amyl, hexyl, and the like. Examples of alkenyl groups include vinyl, allyl, butenyl and the like. Examples of alkynyl groups include ethynyl, propynyl and the like. Examples of cycloalkyl groups include cyclopropyl, cyclobutyl, cyclopentyl, cyclohexyl and the like.

The $C_1$-$C_6$ alkyl group can be unsubstituted, or substituted with one or more substituents selected from the group consisting of hydroxy, alkoxy, aryloxy, alkylaryloxy, heteroaryloxy, oxo, cycloalkyl, phenyl, heteroaryl, heterocyclyl, naphthyl, amino, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, $C_1$-$C_6$ thioalkyl arylthio, or $C_1$-$C_6$ alkylsulfonyl groups. Any substituent can be unsubstituted or further substituted with any one of these aforementioned substituents.

The term "aryl" used herein alone or as part of another group denotes an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups defined hereinabove for alkyl.

The term "$C_1$-$C_6$ alkoxy" used herein alone or as part of another group denotes a $C_1$-$C_6$ alkyl as defined above, linked to an oxygen atom. Examples of an alkoxy groups include but are not limited to methoxy, ethoxy, n-propoxy, isopropoxy, n-butoxy, t-butoxy and the like. The term "phenoxy" as used herein alone or as part of another group denotes a phenyl group linked to an oxygen atom. The $C_1$-$C_6$ alkoxy or phenoxy groups can be unsubstituted or substituted through available atoms with one or more groups defined hereinabove for alkyl.

The term "$C_1$-$C_6$ thioalkyl" used herein alone or as part of another group denotes a $C_1$-$C_6$ alkyl as defined above, linked to a sulfur atom. Non-limiting examples of an thioalkyl groups is thiomethyl, thioethyl, thio-n-propyl, thio-isopropyl, thio-n-butyl, thio-t-butyl and the like. The $C_1$-$C_6$ thioalkyl group can be unsubstituted or substituted through available atoms with one or more groups defined hereinabove for alkyl.

The term "trifluoromethyl" as used herein alone or as part of another group refers to a $CF_3$ group. The term "hydroxy" as used herein alone or as part of another group refers to an OH group. The term "halogen" or "halo" as used herein alone or as part of another group refers to chlorine, bromine, fluorine, and iodine. The term "azido" as used herein alone or as part of another group refers to an $N_3$ group. The term "acetyl" as used herein alone or as part of another group refers to a $COCH_3$ group. The term "nitro" as used herein alone or as part of another group refers to an $NO_2$ group. The term "amino" as used herein alone or as part of another group refers to an $NH_2$ group. The term "sulfonyl" as used herein alone or as part of another group refers to $-S(O)_2-$. Alkylsulfonyl refers to a sulfonyl group linked to an alkyl group as defined above. Arylsulfonyl refers to a sulfonyl group linked to an aryl group as defined above.

In another embodiment, the present invention provides a process for the preparation of fluazinam, represented by formula (3), by reacting compound of formula (1) with a compound of formula (2), wherein one of U and W is amino and the other is a leaving group selected from the group consisting of halogen, alkylsulfonyl and arylsulfonyl in the presence of a base, using MIBK as a reaction solvent.

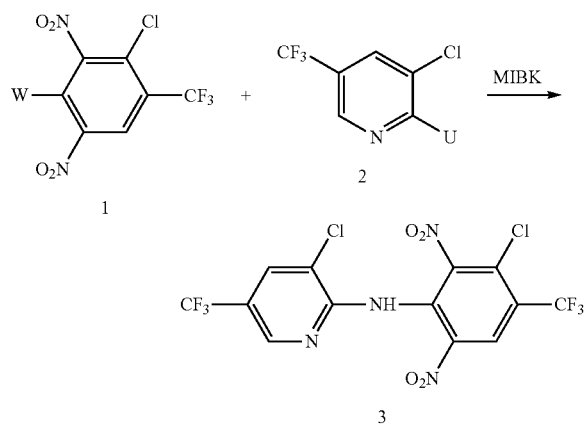

The process of the invention is conducted in a base. Preferably, the base is selected from a group consisting of alkali metal hydroxides (e.g., sodium hydroxide, potassium hydroxide), alkali metal carbonates (e.g., sodium bicarbonate, sodium carbonate, sodium carbonate, potassium carbonate), hydrides (e.g., sodium hydride, potassium hydride), alkaline earth metal hydroxides (e.g., magnesium hydroxide, calcium hydroxide) and alkaline earth metal carbonates (e.g., magnesium carbonate, calcium carbonate). A currently preferred base is either potassium hydroxide or sodium hydroxide.

Preferably, the reagents to solvent ratio is greater than about 10% w/v. More preferably, the reagents to solvent ratio is greater than about 25% w/v, and most preferably the reagents to solvent ratio is greater than about 40% w/v. This provides an advantage over the prior art methods where the dilute reaction conditions (less than 8.2% w/v reagents to solvent) leads to an incomplete consumption of both reactants (A) and (B), thus lowering the yield.

In another embodiment, the present invention provides a process for the preparation of the pyridinamine known as fluazinam, represented by formula (3), by reacting compound of formula (1A) with a compound of formula (2A), using MIBK as a reaction solvent.

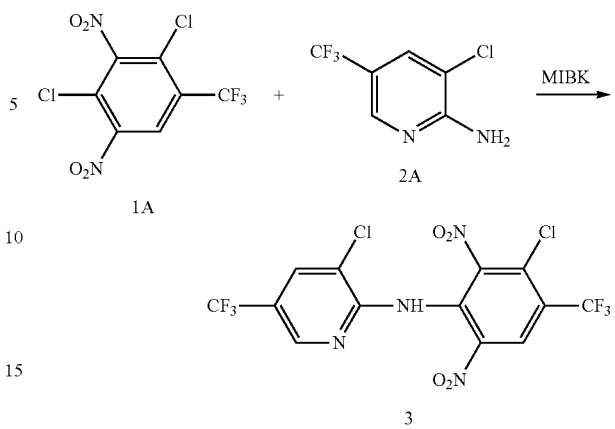

The process of the invention is conducted in a base. Preferably, the base is selected from a group consisting of alkali metal hydroxides (e.g., sodium hydroxide, potassium hydroxide), alkali metal carbonates (e.g., sodium bicarbonate, sodium carbonate, sodium carbonate, potassium carbonate), hydrides (e.g., sodium hydride, potassium hydride), alkaline earth metal hydroxides (e.g., magnesium hydroxide, calcium hydroxide) and alkaline earth metal carbonates (e.g., magnesium carbonate, calcium carbonate). A currently preferred base is either potassium hydroxide or sodium hydroxide.

Preferably, the reagents to solvent ratio is greater than about 10% w/v. More preferably, the reagents to solvent ratio is greater than about 25% w/v, and most preferably the reagents to solvent ratio is greater than about 40% w/v. This provides an advantage over the prior art methods where the dilute reaction conditions (less than 8.2% w/v reagents to solvent) leads to an incomplete consumption of both reactants (A) and (B), thus lowering the yield.

The preferred solvent in the novel process is pure MIBK (e.g., at least about 98% purity) or MIBK in its recycled form containing less than 2% water, preferably less than about 1.9% water, more preferably less than about 1.75% water, most preferably about 1.6% water. In one currently preferred embodiment, the MIBK is in its recycled azeotropic form containing about 1.6% water. MIBK's low water solubility characteristic permits the reaction to be conducted under more concentrated conditions, significantly increasing the efficiency of the reaction.

Generally, due to the exothermic nature of the coupling reaction, the temperature of the reaction is maintained at or below about 0-20° C. for about the first hour. Thereafter, the reaction is allowed to warm up to room temperature (about 25-30° C.), and is stirred at this temperature until completion of the reaction, typically from about 2-3 hours to about 24 hours. The work-up can include acidification, e.g., by adding an acid such as HCl or $H_2SO_4$. A biphasic mixture is formed. The organic layer is then separated and the product is isolated by evaporating the solvent.

Purification of the compounds of formula (1) is afforded by crystallizing said compound from a solvent or a mixture of solvents, preferably an organic solvent or a mixture of organic solvents. Thus, in one embodiment, the present invention provides a process for purifying a compound of formula (1), by crystallizing said compound from a solvent or a mixture of solvents. In one embodiment, the compound of formula (I) is fluazinam, represented by the structure of formula (3). A currently preferred organic solvent in the crystallization step is ethanol. Suitable grades of ethanol include 80-100% ethanol. The ethanol can be wet or dry.

Crystallization is performed as known in the art, for example by mixing the desired compound in an appropriate amount of solvent or mixture of solvents, heating to achieve dissolution, and cooling to precipitate the product. Alternatively, the compound is dissolved in one solvent, and a second solvent in which the compound is insoluble or slightly soluble is added, until precipitation is achieved. Also, the reaction can be seeded with the appropriate compound in order to induce crystallization, as known in the art.

As contemplated herein, the crystallization methods described herein may result in the formation of one or more of novel polymorphic forms of fluazinam, or mixtures thereof. Thus, in another aspect, the present invention is generally directed to a novel crystalline polymorphic forms of fluazinam referred to herein as "polymorph Form I" and "polymorph Form II", and to mixtures of said polymorphs. The present invention also provides methods for preparing the novel polymorphs, as well as to pharmaceutical compositions comprising same, and methods of use thereof for combating noxious livings on agricultural and horticultural crops.

Solids exist in either amorphous or crystalline forms. In the case of crystalline forms, molecules are positioned in 3-dimensional lattice sites. When a compound recrystallizes from a solution or slurry, it may crystallize with different spatial lattice arrangements, a property referred to as "polymorphism," with the different crystal forms individually being referred to as a "polymorph". Different polymorphic forms of a given substance may differ from each other with respect to one or more physical properties, such as solubility and dissociation, true density, crystal shape, compaction behavior, flow properties, and/or solid state stability. In the case of a chemical substance that exists in two (or more) polymorphic forms, the unstable forms generally convert to the more thermodynamically stable forms at a given temperature after a sufficient period of time. When this transformation is not rapid, the thermodynamically unstable form is referred to as the "metastable" form. In general, the stable form exhibits the highest melting point, the lowest solubility, and the maximum chemical stability. However, the metastable form may exhibit sufficient chemical and physical stability under normal storage conditions to permit its use in a commercial form. Furthermore, the metastable form, although less stable, may exhibit properties desirable over those of the stable form, such as better formulative ability, improved dispersability in water and the like.

In the case of fluazinam, no known crystalline forms are known. The inventors of the present applications, after extensive experimentation, have discovered two new crystalline Forms of fluazinam, designated Form I and Form II. These two crystalline forms exhibit different spectral characteristics as depicted by their distinct Differential Scanning calorimetry (DSC) thermograms, X-ray diffraction patterns, and infrared (IR) spectra.

Form I

In one embodiment, the present invention provides a novel crystalline polymorphic form of 3-chloro-N-(3-chloro-5-trifluoromethyl-2-pyridyl)-α,α,α-trifluoro-2,6-dinitro-p-toluidine (fluazinam), designated "Form I". This novel and surprising polymorph may be characterized by, for example, by DSC, X-Ray powder diffraction spectrometry and/or IR spectrometry.

For example, as shown in FIG. 1, Form I exhibits an X-ray powder diffraction pattern having characteristic peaks (expressed in degrees 2θ+/−0.2°θ) at one or more of the following positions: 8.7, 10, 12.0, 13.7, 14.5, 17.4, 18.5, 19.7, 21.8, 22.9, and 30.2. The X-Ray powder diffraction were collected on Philips powder diffractometer PW1050/70 operated at 40 kV and 30 mA using CuKα radiation (wavelength equal to 1.54178 Å) and diffracted beam graphite monochromator. The typical θ-2θ scan range is 3-35° 2 Theta with a step size of 0.05° and a count time of 0.5 seconds per step.

The samples were grinded using agate mortar and pestle. The obtained powder is then pressed into aluminum sample holder with rectangular cavity of 20 mm*15 mm and of 0.5 mm depth.

Figure 2:
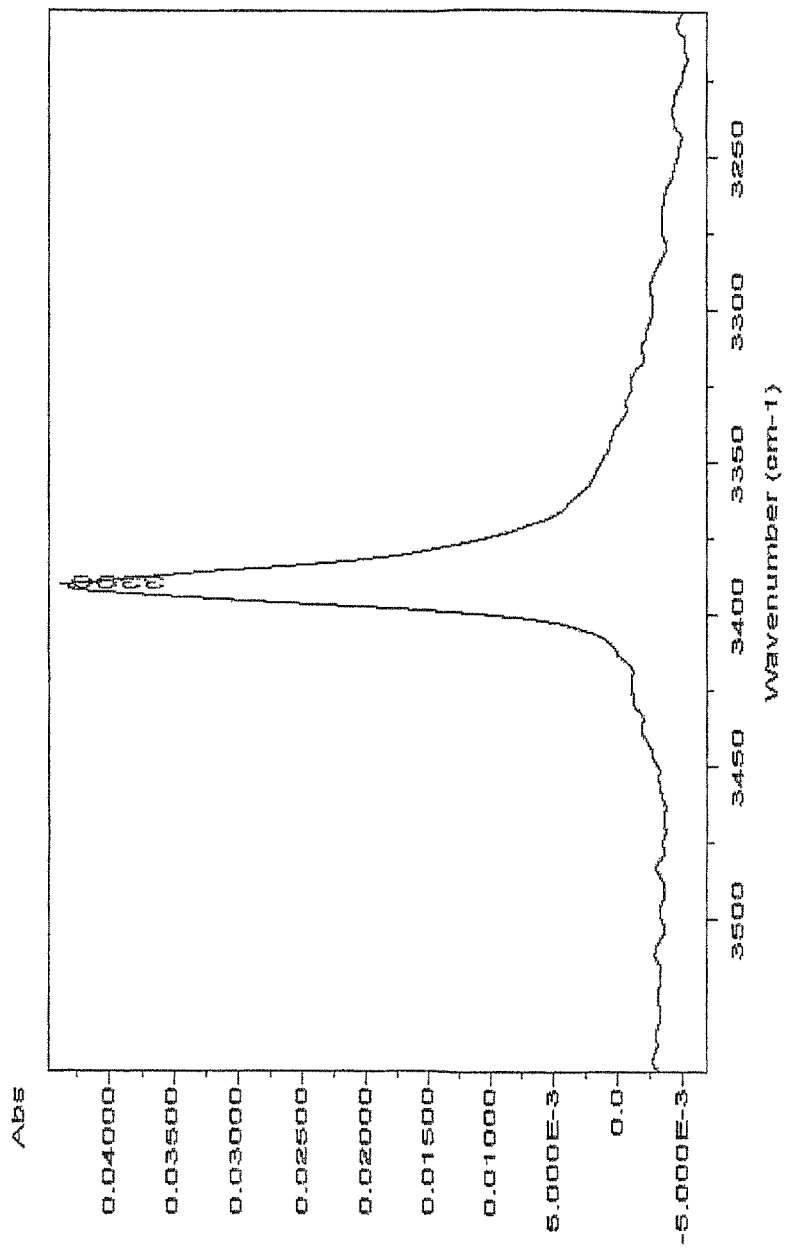
FIG. 2: is a FT Infrared spectrum of fluazinam Form I (at the 3000 cm$^{-1}$ range).

Furthermore, as shown in FIG. 2 (showing the 3000 cm$^{-1}$ range only), Form I also exhibits an Infrared (IR) spectrum having a characteristic peak at 3390 cm$^{-1}$, as measured by a Fourier transform infrared (FT-IR) spectrophotometer ReactIR™ 1000 of Mettler Toledo Autochem (ATR method, MCT detector), diamond window, in DuraSamplIR™ sampling device. The diamond sensor has a standard focusing optic of ZnSe. The powdered samples were compressed in the sampling device and were measured with resolution of 4 cm$^{-1}$ and 256 scans.

Figure 3:
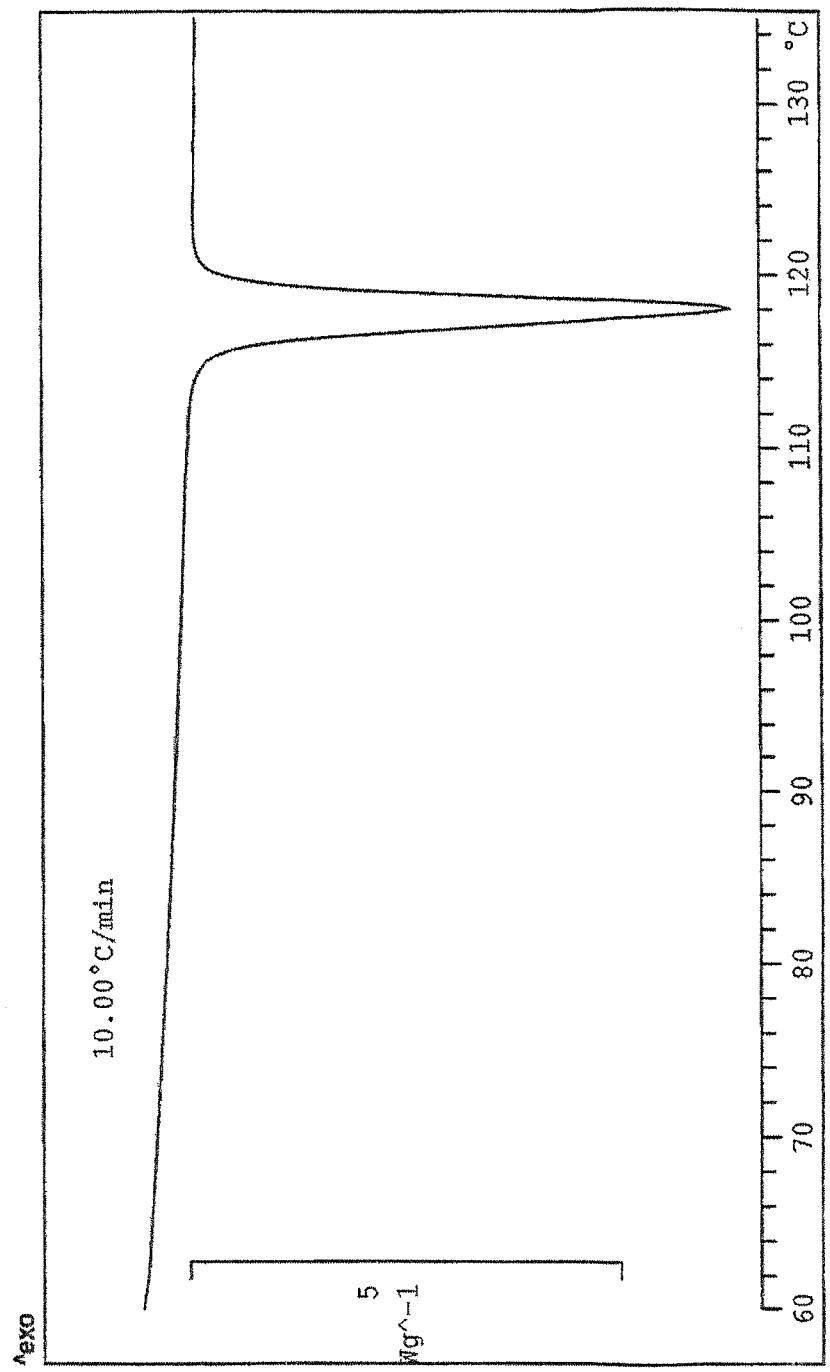
FIG. 3: is a Differential Scanning Calorimetry (DSC) thermogram of fluazinam Form I.

Furthermore, as shown in FIG. 3, Form I also exhibits a Differential Scanning calorimetry (DSC) thermogram which is characterized by a predominant endotherm peak at about 115.5° C. as measured by DSC of Mettler Toledo with 821$^e$ module. The weighted samples (2-4 mg) were purged with nitrogen flow during the measurements at a scan rate of 2 and/or 10° C. per minute. Aluminum standard pierced crucibles of 40 μL were used. The evaluation is performed using STAR$^e$ software. As used herein, the term "about 115.5° C." means a range of 114° C. to 117° C. In this regard, it should be understood that the endotherm measured by a particular differential scanning calorimeter is dependent upon a number of factors, including the rate of heating (i.e., scan rate), the calibration standard utilized, instrument calibration, relative humidity, and upon the chemical purity of the sample being tested. Thus, an endotherm as measured by DSC on the instrument identified above may vary by as much as ±1.5° C.

Form I generally crystallizes in the form of prisms, typically as large yellow prisms, as described herein.

In another aspect, the present invention provides processes for preparing the novel fluazinam polymorph Form I. Form I can be prepared by dissolving fluazinam in an appropriate amount of solvent or mixture of solvents, heating to achieve dissolution, and cooling to precipitate the product. Alternatively, fluazinam is dissolved in one solvent in which it is soluble, and a second solvent (anti-solvent) in which the compound is insoluble or slightly soluble is added, until precipitation is achieved. Also, the reaction can be seeded with Form I seeds in order to induce crystallization, as known in the art.

The fluazinam starting material used for preparing Form I can be any form of fluazinam, including fluazinam prepared in accordance with U.S. Pat. No. 4,331,670, amorphous fluazinam, fluazinam Form II, a mixture of fluazinam Form I and Form II, or any other fluazinam known in the art.

For example, in one embodiment, Form I can be prepared by crystallizing fluazinam from a solvent selected from the group consisting of ethanol, acetonitrile, methylene chloride and n-hexane; and isolating the resulting crystals. In a currently preferred embodiment, the process includes preparing a solution of fluazinam in one or more of the aforementioned solvents, preferably by applying heat until dissolution is complete, and cooling the solution until crystals appear. Generally, cooling the solution to room temperature (defined herein as about 20° C. to about 25° C.) is sufficient, however, the solution can be cooled to lower temperatures, for example 0° C., 5° C., 10° C., 15° C. and the like. The crystals are then isolated by any conventional method known in the art, for example by filtration, centrifugation, etc.

Form I can also be prepared by crystallizing fluazinam from diethyl ether, by dissolving fluazinam in diethyl ether, preferably at room temperature, and the flask is left to stand partially open so that the solvent slowly evaporates. Gradually, crystals begin to appear, typically in the form of large yellow prisms, which are then isolated in a conventional manner. Generally, only a part of the solvent evaporates before the crystals begin to appear, for example about 10-90% of the solvent evaporates in the air, leading to the appearance of Form I crystals.

Form II

In another embodiment, the present invention provides a novel crystalline polymorphic form of 3-chloro-N-(3-chloro-5-trifluoromethyl-2-pyridyl)-α,α,α-trifluoro-2,6-dinitro-p-toluidine (fluazinam), designated "Form II". This novel and surprising polymorph may be characterized by, for example, by DSC, X-Ray powder diffraction spectrometry and/or IR spectrometry.

Figure 4:
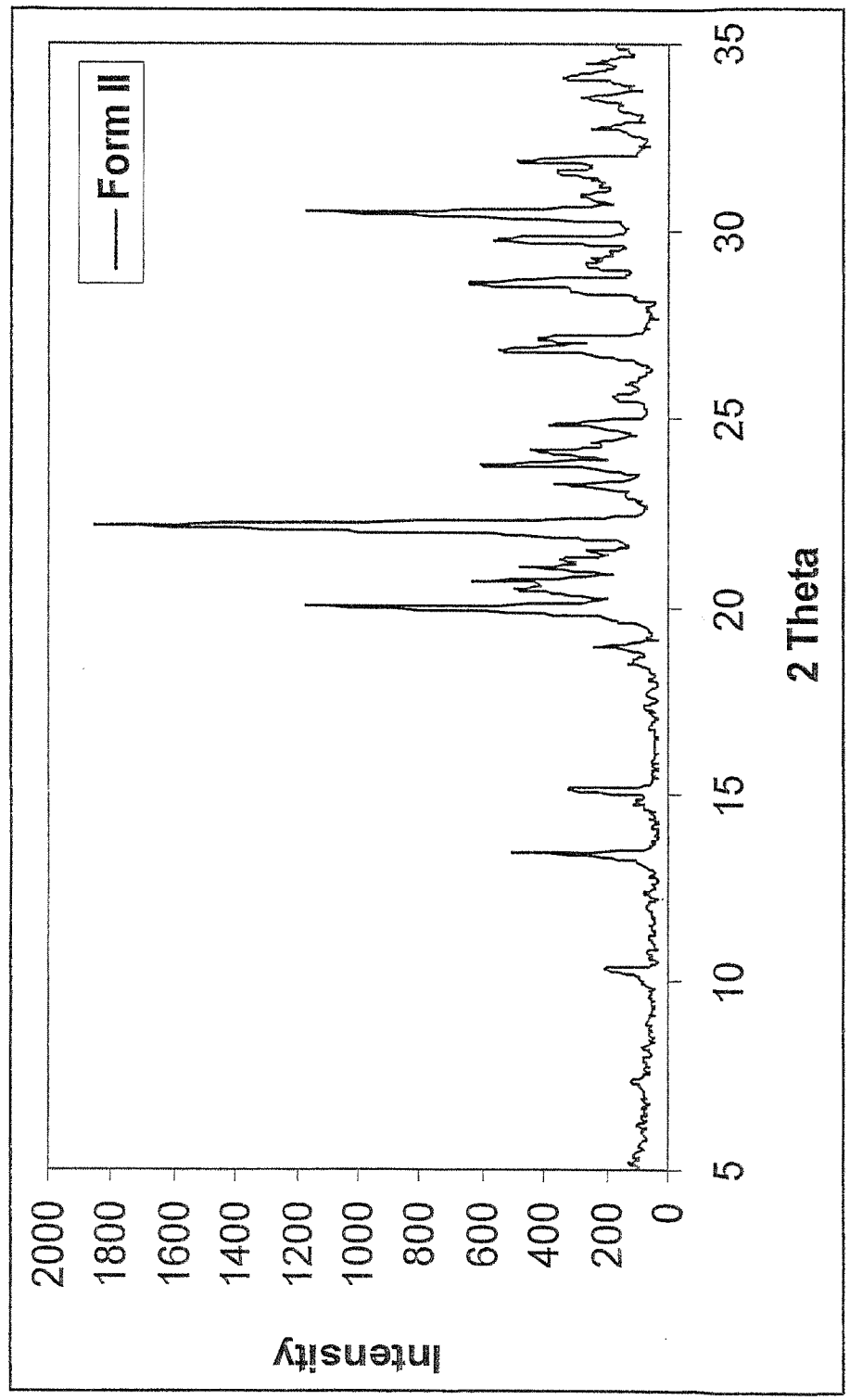
FIG. 4 is an X-ray powder diffraction spectrum of fluazinam Form II.

For example, as shown in FIG. 4, Form II exhibits an X-ray powder diffraction pattern having characteristic peaks (expressed in degrees 2θ (+/−0.2°θ) at one or more of the following positions: 7.4, 10.4, 13.4, 15.1, 18.95, 20, 20.4, 21.05, 21.3, 22.2, 24.9, 27.15, 28.6, and 30.5. The X-Ray powder diffraction was measured as described above.

Figure 5:
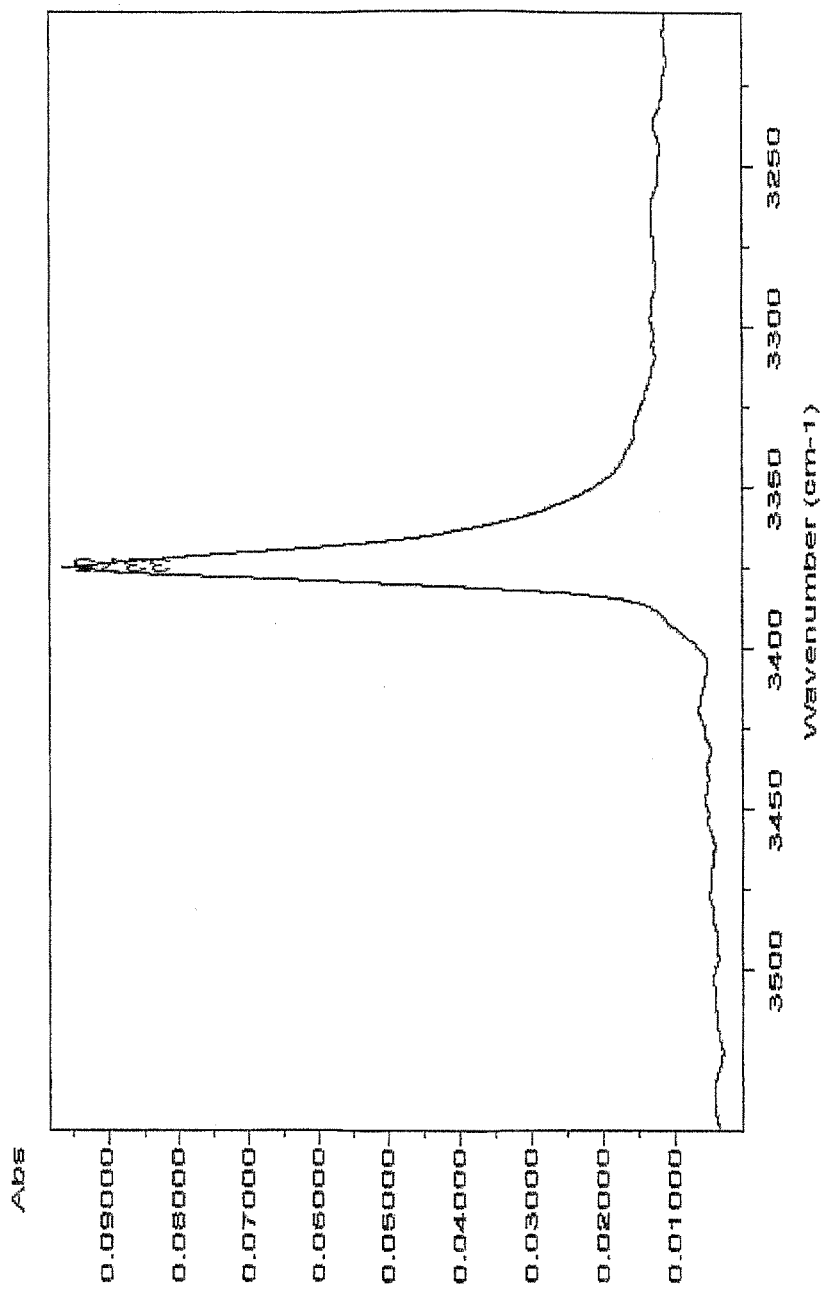
FIG. 5: is a FT Infrared spectrum of fluazinam Form II (at the 3000 cm$^{-1}$ range).

Furthermore, as shown in FIG. 5 (showing the 3000 cm$^{-1}$ range only), Form II also exhibits an Infrared (IR) spectrum having a characteristic peak at about 3375 cm$^{-1}$, as measured by a Fourier transform infrared (FT-IR) spectrophotometer as described above.

Figure 6:
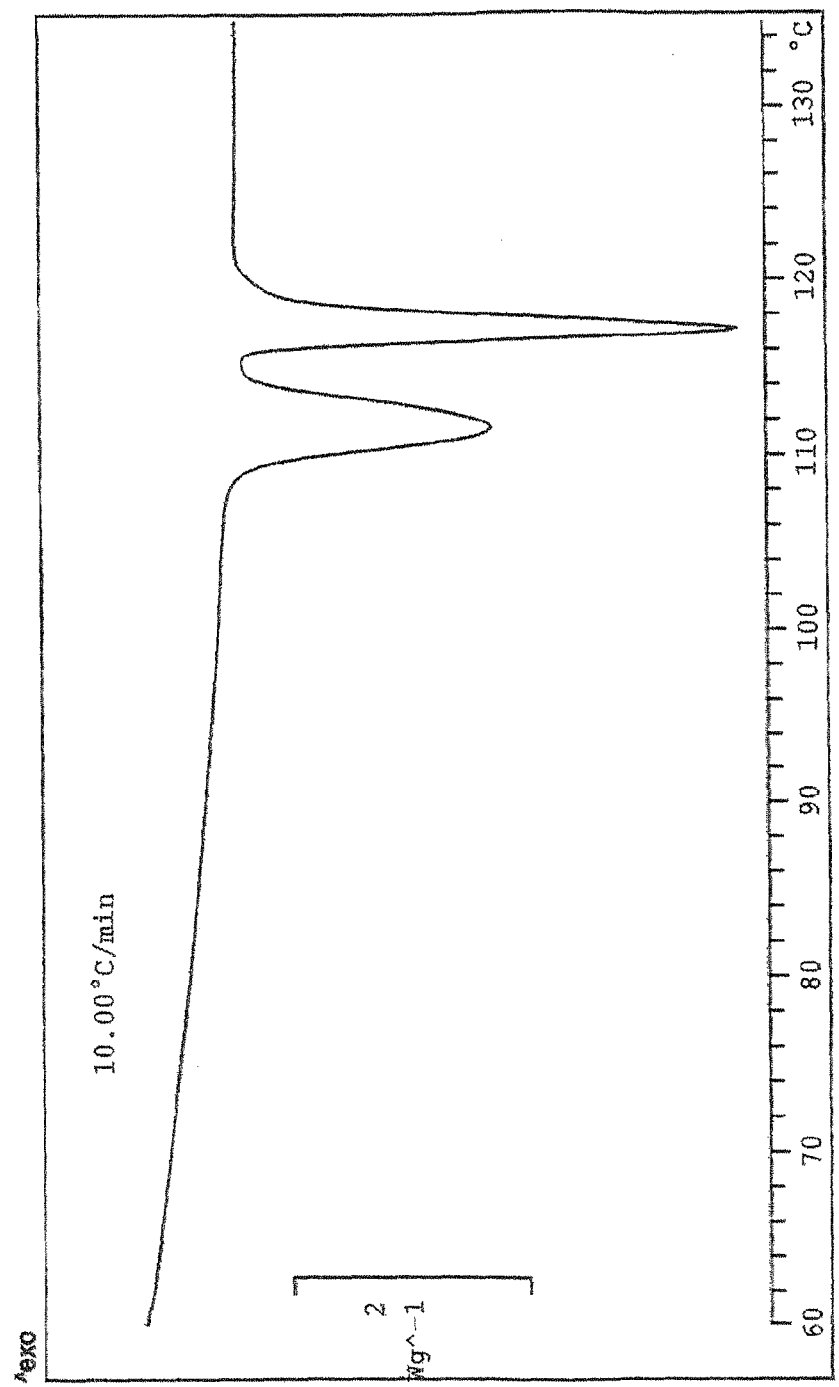
FIG. 6: is a Differential Scanning Calorimetry (DSC) thermogram of fluazinam Form II.

Furthermore, as shown in FIG. 6, Form II also exhibits a DSC thermogram which is characterized by monotropic system showing a predominant endotherm at about 109° C. (Form II to liquid). The thermogram further shows an endotherm at about 115.5° C. resulting from crystallization to Form I. The thermogram was measured by a Differential Scanning Calorimeter as described above. As used herein, the term "about 109° C." means from about 107.5° C. to about 110.5° C.

Form II generally crystallizes in the form of needles, typically as bright yellow needles.

In another aspect, the present invention provides processes for preparing the novel polymorph Form II. Form II can be prepared by dissolving fluazinam in an appropriate amount of solvent or mixture of solvents, heating to achieve dissolution, and cooling to precipitate the product. Alternatively, fluazinam is dissolved in one solvent in which it is soluble, and a second solvent (anti-solvent) in which the compound is insoluble or slightly soluble is added, until precipitation is achieved. Also, the reaction can be seeded with Form II seeds in order to induce crystallization, as known in the art.

The fluazinam starting material used for preparing Form II can be any form of fluazinam, including fluazinam prepared in accordance with U.S. Pat. No. 4,331,670, amorphous fluazinam, fluazinam Form I, a mixture of fluazinam Form I and Form II, or any other fluazinam known in the art.

For example, Form II can be prepared by crystallizing fluazinam from diethyl ether, preferably at room temperature, and rapidly evaporating the solvent. This leads to the formation of crystals, typically in the form of bright yellow needles, which are then isolated in a conventional manner.

Form II can also be prepared by preparing a solution of fluazinam in ethanol; by preparing a solution of fluazinam in ethanol as described above with respect to Form I. However, instead of cooling to precipitate the product, the solution is exposed to the environment, so that part of the solvent slowly evaporates. Gradually, crystals begin to appear, typically in the form of bright yellow needles, which are then isolated. Generally, only a part of the solvent evaporates before the crystals begin to appear, for example about 10-90% of the solvent evaporates in the air, leading to the appearance of Form II crystals.

Form I and Form II Mixtures

In yet another embodiment, the present invention provides a mixture of polymorphic Form I and Form II of 3-chloro-N-(3-chloro-5-trifluoromethyl-2-pyridyl)-α,α,α-trifluoro-2,6-dinitro-p-toluidine (fluazinam).

Figure 7:
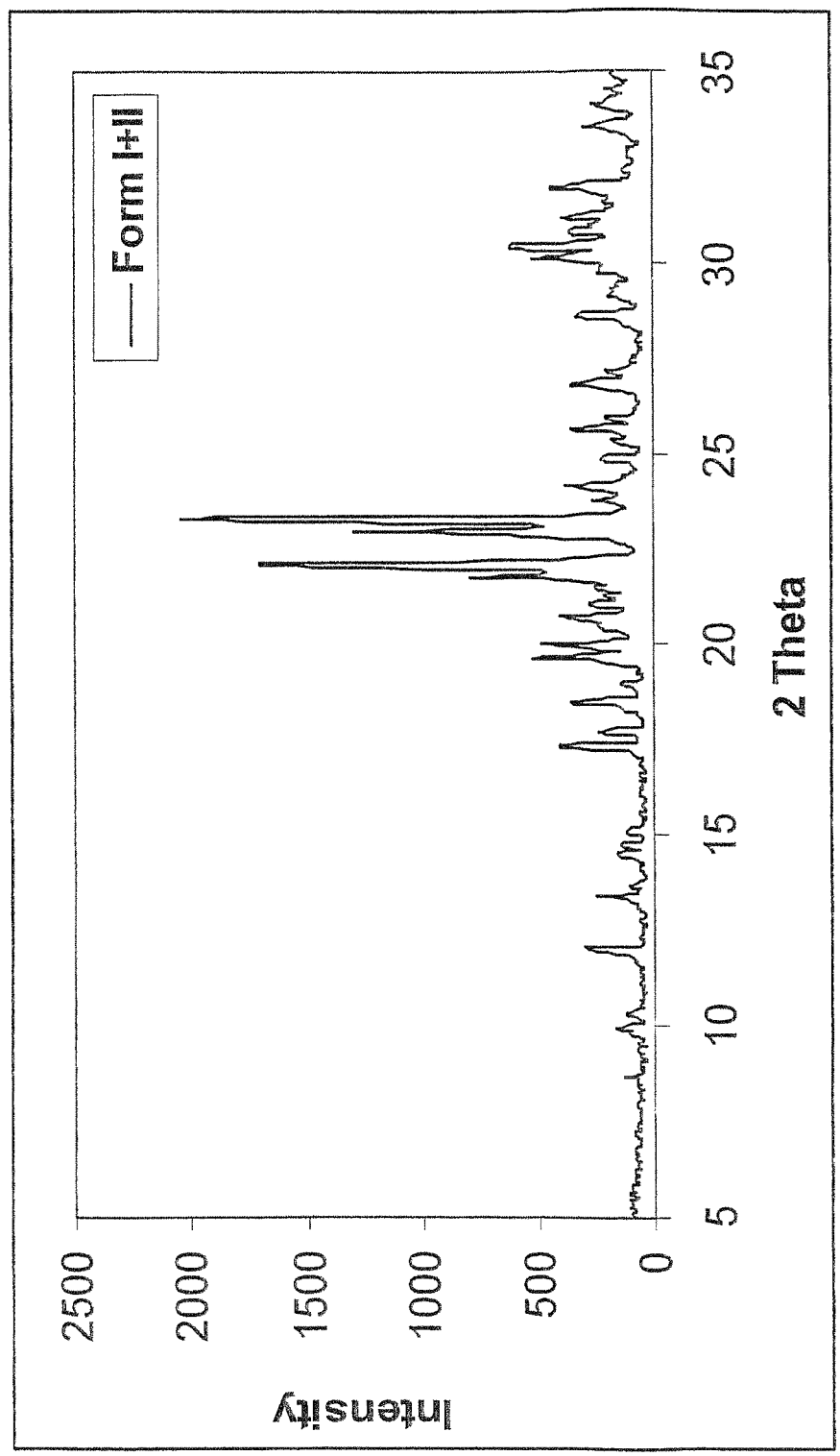
FIG. 7 is an X-ray powder diffraction spectrum of a fluazinam Form I and II mixture.
Figure 8:
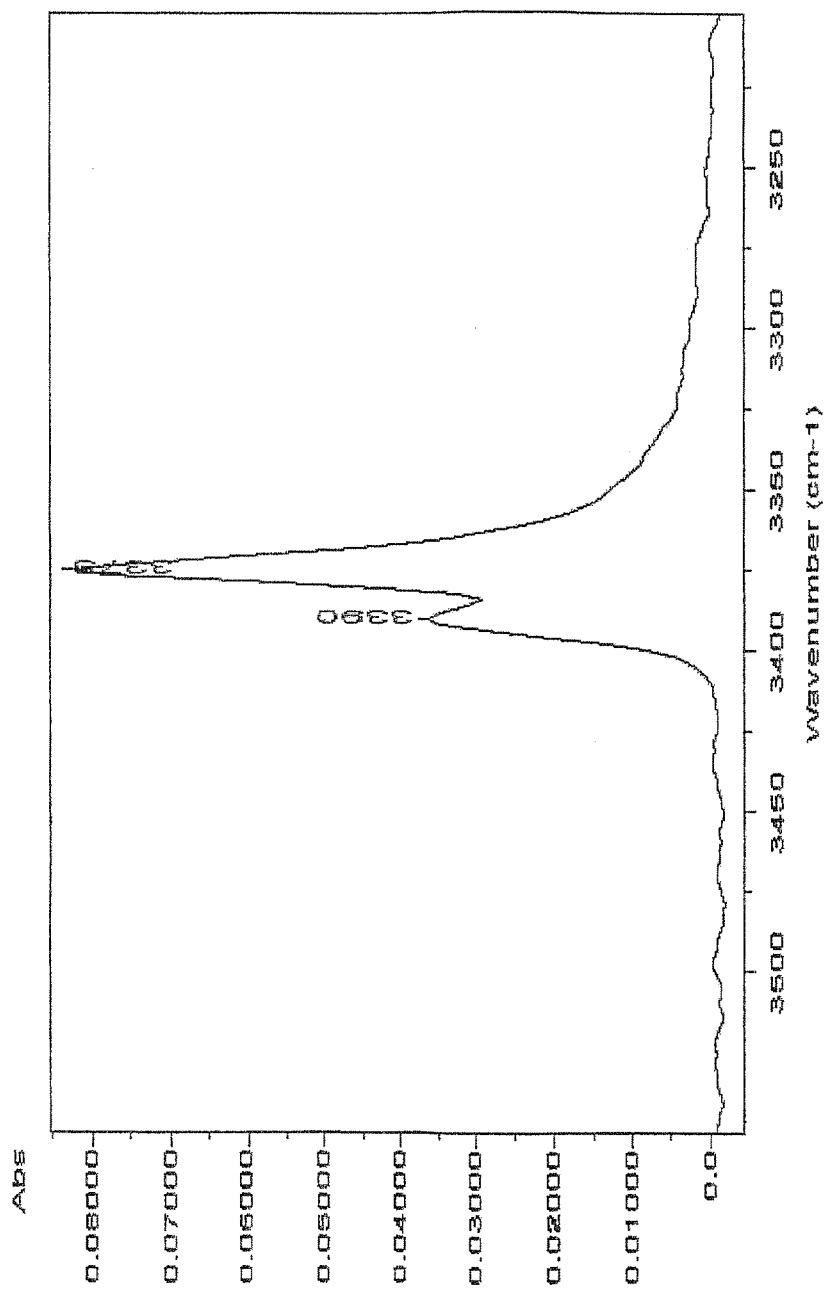
FIG. 8: is a FT Infrared spectrum of a fluazinam Form I and II mixture (at the 3000 cm$^{-1}$ range).
Figure 9:
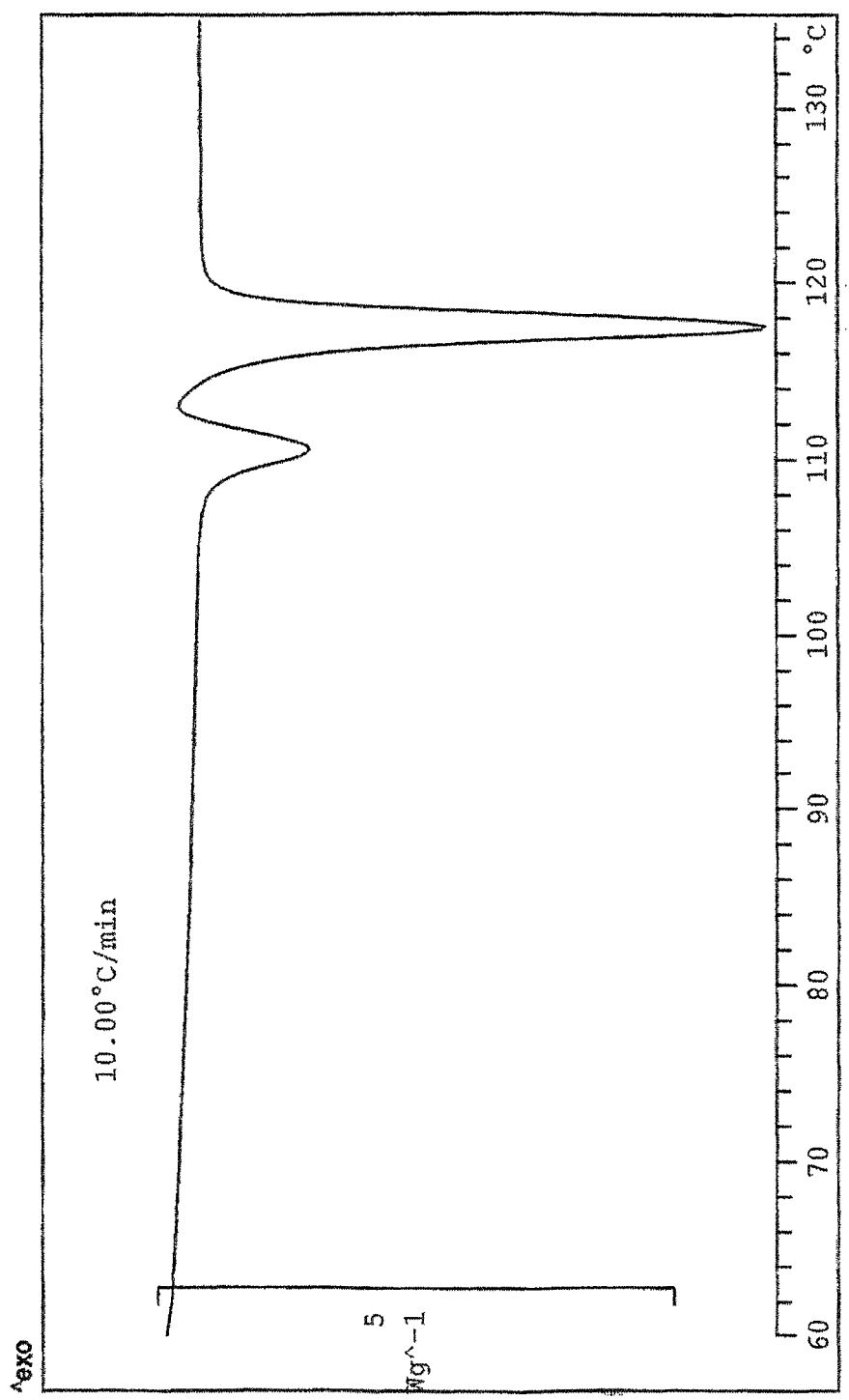
FIG. 9: is a Differential Scanning calorimetry (DSC) thermogram of a fluazinam Form I and II mixture.

The mixture exhibits an X-ray powder diffraction pattern substantially as shown in FIG. 7. Further, the mixture exhibit an infrared (IR) spectrum substantially as shown in FIG. 8 (showing the 3000 cm$^{-1}$ range only). Further, the mixture exhibits a Differential DSC thermogram substantially as shown in FIG. 9, as measured by Differential Scanning Calorimeter as described above.

The fluazinam starting material used for preparing the Form I and Form II mixture can be any form of fluazinam, including fluazinam prepared in accordance with U.S. Pat. No. 4,331,670, amorphous fluazinam, fluazinam Form I, fluazinam Form II, or any other fluazinam known in the art.

A mixture of Form I and Form II can simply be prepared by mixing polymorphic Form I and Form II to obtain a mixture. However, the mixture can also be prepared by crystallizing fluazinam from a solvent selected from the group consisting of isopropyl alcohol, n-hexane and toluene; and isolating the resulting crystals. In a currently preferred embodiment, the process includes preparing a solution of fluazinam in one or more of the aforementioned solvents, preferably by applying heat until dissolution is complete, cooling the solution until crystals appear, and isolating the crystals. Generally, cooling the solution to room temperature is sufficient, however, the solution can be cooled to lower temperatures, for example 0° C., 5° C., 10° C., 15° C. and the like.

The mixture of Form I and Form II can also be prepared by dissolving fluazinam in a solvent in which said compound is soluble, adding an anti-solvent, and isolating the resulting crystals. In one currently preferred embodiment, the solvent is acetone. In another currently preferred embodiment, the anti-solvent is water.

Compositions and Uses

Fluazinam is known impart excellent effect for combating noxious livings such as insects, mites, fungi and bacteria, for example, excellent antifungal and antibacterial effect for controlling noxious fungi and bacteria multiplicating on industrial products, seeds and fruits in storage such as *Aspergillus* sp. *Gibberella* sp. and *Penicillium* sp.

Fluazinam is also effective for controlling noxious living grown on agricultural and horticultural crops and up-land, for example, insects such as Lepidoptera as *Plutella Xylostella, Mamestra brassicae* and *Spodoptera litura*; Hemiptera as *Nephotettix cincticeps* and *Delphacodes striatella*; Coleoptera as *Callosobruchus chimensis* and *Epilachna vigintioctopunctata*; and Diptera such as *Musca domestica* and *Culexopipiens pallens*; and mites such as *Tetranychus urticae, Tetranychus telarius* and *Panonychus citri*; and fungi and bacteria for plants such as *Pyricularia oryzae, Rhizoctonia solani, Collectotrichum lagenarium, Pseudopernospora cubensis, Sphaerotheca fuliginea, Phytophthora infestans, Diaporthe citri, Alternaria solani, Venturia inaequalis, Plasmopara viticola, Botrytis cinerea, Puccinia recondita* and *Sclerotinia sclerotiorum*.

Fluazinam also imparts excellent effect for controlling various noxious livings especially noxious fungi to agricultural and horticultural plants.

Thus, in one embodiment, the present invention also provides compositions comprising the novel crystalline polymorphs, which are useful for controlling and combating noxious living grown on agricultural and horticultural crops and up-land, for example insects, mites, fungus and bacteria. In one embodiment, the composition comprises a crystalline polymorph Form I of fluazinam; and an acceptable adjuvant. In another embodiment, the composition comprises a crystalline polymorph Form II of fluazinam and an acceptable adjuvant. In yet another embodiment, the composition comprises a mixture of a crystalline polymorph Form I and Form II of fluazinam; and an acceptable adjuvant.

The present invention also relates to methods for combating insects, mites, fungus and bacteria, comprising applying to the insects, mites, fungus or bacteria an effective amount of the compositions of the invention.

The present invention also relates to methods for protecting crops and upland, including industrial products thereof, such as seeds and fruits, by applying to the crops or products thereof an effective amount of the compositions of the invention.

The concentration of the fluazinam polymorphs for use in the compositions of the present invention will depend upon object noxious livings, the method of application, and the form of the composition and the dose of the active ingredient. The concentration is not critical and it is usually in a range of about 1 to 10,000 ppm, preferably about 20 to 2,000 ppm.

The composition can be prepared in a variety of forms such as dust, wettable powder, emulsifiable concentrate, inert emulsion, oil solution, aerosol preparation, etc. with adjuvants as the cases of agricultural compositions. The composition can be applied with or without diluting them in suitable concentrations.

Suitable adjuvants include powdery carries such as talc, kaolin, bentonite, diatomaceous earth, silicon dioxide, clay and starch; liquid diluents such as water, xylene, toluene, dimethylsulfoxide, dimethylformamide, acetonitrile, and alcohol; emulsifiers dispersing agents, surfactants such as sodium alkyl benzene sulfonate, polyoxyethylene alkylaryl ether, sodium naphthalene sulfonate formaldehyde condensate, calcium ether sulfate, polyoxyethyleneglycol dodecylphenyl ether, polyoxyethylene lauryl ether, polyoxyethylene fatty acid ester, sodium alkylsulfate, sulfate of polyoxyethylene alkylaryl ether and di-alkylsulfosuccinate etc.

The concentration of the active ingredient in the insecticidal acaricidal, fungicidal or bactericidal composition is usually 5 to 80 wt. % in the case of the oily concentrate; and 0.5 to 30 wt. % in the case of dust; 5 to 60 wt. % in the case of wettable powder. It is also possible to combine with the other agricultural ingredients such as the other insecticides, acaricides, and/or plant growth regulators. Sometimes synergistic effects are found. The other agricultural ingredients include organic phosphoric acid ester type compounds, carbamate type compounds, dithio (or thiol) carbamate type compounds, organic chlorine type compounds, dinitro type compounds, organic sulfur or organometallic type compounds, antibiotics, substituted diphenyl ether type compounds, urea type compounds, triazine type compounds, benzoylurea type compounds, pyrethroid type compounds, imide type compounds and benzimidazole type compounds and more particularly, benzoylurea type insecticides such as N-(2,6-difluorobenzoyl)-N'-(p-chlorophenyl)urea; pyrethroid type insecticides such as .alpha.-cyano-3-phenoxybenzyl-2-(4-chlorophenyl) isovalerate; imide type germicides such as N-(3,5-dichlorophenyl)-1,2-dimethylcyclopropane-1,2-dicarboximide; benzimidazole type germicides such as methyl-1-(butylcarbamoyl)-2-benzimidazolecarbamate; thiocarbamate type germicides such as S-ethyl N-(3-dimethylaminopropyl)thiocarbamate hydrochloride; dithiocarbamate type germicides such as manganese ethylenebisdithiocarbamate; and urea type germicides such as 2-cyano-N-(ethylaminocarbonyl)-2-(methoxyimino)acetamide.

The following examples are presented in order to more fully illustrate certain embodiments of the invention. They should in no way, however, be construed as limiting the broad scope of the invention. One skilled in the art can readily devise many variations and modifications of the principles disclosed herein without departing from the spirit and scope of the invention.

EXPERIMENTAL SECTION

The following abbreviations are used herein:
ACP—2-amino-3-chloro-5-trifluoromethylpyridine
ACN—acetonitrile
CNB—2,4-dichloro-3,5-dinitrobenzotrifluoride
DMF—dimethylformamide
DMSO—dimethylsulfoxide
EtOH—ethanol
MEK—methylethylketone
MIBK—methylisobutylketone
THF—Tetrahydrofuran Example 1

Solvent Effect

Fluazinam was prepared by coupling compounds 1A and 2A in several organic solvents, as shown in the Scheme below. 1.5 gr. (1), 2.5 gr. (2)—5% excess, 1.5 gr. KOH (s)—3 eq. in 10 ml solvent were inserted into a 25 ml round flask with magnetic stirring. The mixture was stirred at 30° C. and samples were taken sequentially until the reaction terminated.

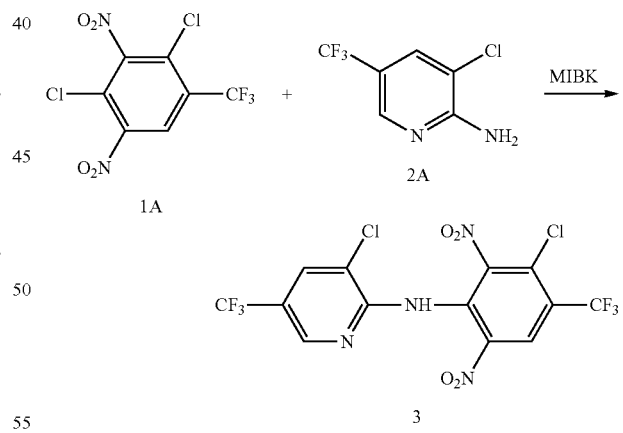

Table 2 shows the effects of various solvents in pure and azeotrope form on the synthesis of fluazinam:

TABLE 2

The effects of various solvents in pure and azeotrope form

| Solvent | (%) Impurity[a] | (%) 4[b] | (%) 1A[c] | (%) 2A[d] | (%) 3 |
|---|---|---|---|---|---|
| Acetonitrile | 3.7% | 6.5% | 3.1% | 0.0% | 86.7% |
| Acetonitrile-84% | 4.6% | 15.8% | 2.5% | 8.1% | 69.0% |

TABLE 2-continued

The effects of various solvents in pure and azeotrope form

| Solvent | (%) Impurity[a] | (%) 4[b] | (%) 1A[c] | (%) 2A[d] | (%) 3 |
|---|---|---|---|---|---|
| THF | 2.8% | 7.2% | 2.5% | 0.0% | 87.5% |
| THF-95% | 1.9% | 8.0% | 2.8% | 2.0% | 85.3% |
| MIBK | 3.8% | 1.2% | 2.0% | 1.0% | 92.0% |
| MIBK-98% | 2.2% | 1.8% | 2.8% | 1.1% | 92.1% |
| MEK | 8.1% | 3.3% | 2.4% | 3.6% | 82.6% |
| MEK-88% | 5.3% | 9.0% | 2.5% | 10.3% | 72.9% |
| DMF | 16.7% | 8.5% | 2.3% | 3.6% | 68.9% |
| DMSO | 8.6% | 14.1% | 11.1% | 2.0% | 64.2% |

[a] = total impurities identified in reaction, except impurity 4.
[b] = percent of hydrolysis by-product 4.
[c] = unreacted regent 1A.
[d] = unreacted regent 2A.

The results show that:
1. MIBK in both its pure and wet forms shows superiority over the other solvents both in yield and purity.
2. MIBK is the only solvent where the azeotrope form performance is not reduced compare to its pure form.
3. The azeotrope form of all the solvents other than MIBK exhibit high tendency towards formation of hydrolysis product 4.
4. DMF and DMSO exhibit an exceptionally high degree of impurities and are therefore not suitable for this process.

Example 2

Synthetic Procedure (0.3 mol Scale)

Raw materials 1A, CNB, and 2A, ACP, are synthesized in the following manner:
Raw Material 1A:

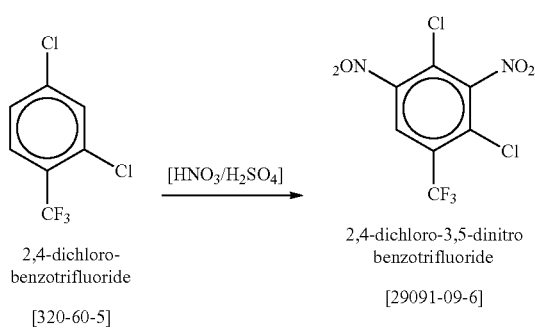

Raw Material 2A:

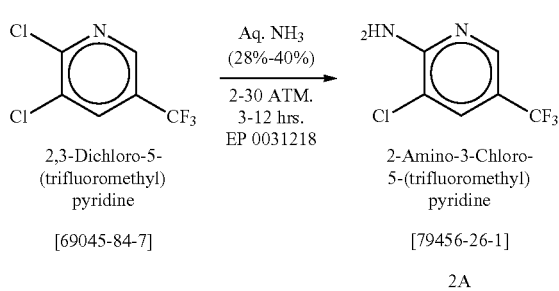

Synthesis of Fluazinam

To a three necked, oil loop reactor equipped with a thermometer and a condenser the following reagents were added sequentially: 60 gr. ACP (=0.3 mol), 95 gr. of CNB powder (3% mol excess) and 340 gr. MIBK azeotrope (containing 1.6% water) and cooled to 20-25° C.

While still at low temperature 70 gr. of KOH(s) (=3.5 mol eq.) were added sequentially 10 gr. every 20 minutes, while preventing the temperature from rising above 30° C. The mixture is stirred further after the addition (at room temperature 25-30° C.) until there is no further consumption of reagents (as determined by HPLC).

The mixture is acidified by the addition of 400 g of HCl-5% and washed with 400 gr. NaCl-5% solution. Upon acidification of the aqueous layer of this bi-phasic mixture, the organic phase is separated using a funnel and, the solvent is evaporated in vacuum to dryness.

The resulting crude material is approximately 150 gr. of yellow fluazinam product, with a purity of ca. 95% and the chemical yield approximately 98%.

The crude product is crystallized in hot ethanol to obtain approximately 140 gr. of a yellow powdery product with purity above 98% and a total yield of 90%.

Example 3

Preparation of Fluazinam Form I 2 g. of fluazinam were heated in 10 g. of ethanol until complete dissolution.

The solution was then cooled to room temperature. Yellow crystals were filtered out and dried at 40° C. in oven. The crystals were characterized as fluazinam Form I.

Example 4

Preparation of Fluazinam Form I 15 g. of fluazinam and 10 g. of acetonitrile were heated until complete dissolution, and then cooled to room temperature. The yellow crystals were filtered and dried at 40° C. The crystals were characterized as fluazinam Form I.

Example 5

Preparation of Fluazinam Form I 2 g. of fluazinam were dissolved in 10 g. of methylene chloride while applying low heating over a heating plate. The heated solution was stirred over the heating plate until crystals were obtained. The yellow crystals were filtered and dried at 40° C. The crystals were characterized as fluazinam Form I.

Example 6

Preparation of Fluazinam Form I 2 g. of fluazinam and 30 g. of n-hexane were heated up until complete dissolution was reached. Then the solution was cooled to room temperature, and the crystals were filtered and dried at 40° C. The crystals were characterized as fluazinam Form I.

Example 7

Preparation of Fluazinam Form I 2 g. of fluazinam were dissolved in 10 g. of diethyl ether at room temperature. Slow evaporation of the solvent (the flask was left partially open at room temperature) enabled large, yellow prisms to appear. The crystals were filtered and dried at 40° C. The crystals were characterized as fluazinam Form I.

Example 8

Preparation of Fluazinam Form II 2 g. of fluazinam were dissolved in 10 g. of diethyl ether as described in Example 5. The solvent was rapidly evaporated from the flask and bright yellow needles appeared. The crystals were collected from the flask and dried at 40° C. The crystals were characterized as fluazinam Form II.

Example 9

Preparation of Fluazinam Form II 2 g. of fluazinam were heated in 10 g. of ethanol as described in example 1, except that the flask was left open and part of the ethanol evaporated from the solution. The crystallization was faster and bright yellow needles appeared in the bottom of the flask. The crystals were filtered and dried at 40° C. The crystals were characterized as fluazinam. Form II.

Example 10

Preparation of a Mixture of Fluazinam Form I and Form II 3 g. of fluazinam and 10 g. of Isopropyl alcohol were heated until complete dissolution. The solution was slowly cooled to room temperature. Yellow crystals were filtered and dried at 40° C. The crystals were characterized as a mixture of fluazinam Form I and Form II.

Example 11

Preparation of a Mixture of Fluazinam Form I and Form II 6 g. of fluazinam and 6 g. of toluene were heated up until complete dissolution. The solution was cooled to 0° C. with water-ice bath. The crystals were filtered and dried at 40° C. The crystals were characterized as a mixture of fluazinam Form I and Form II.

Example 12

Preparation of a Mixture of Fluazinam Form I and Form II 10 g. of fluazinam were dissolved in 10 g. of acetone at room temperature. A few drops of water were added as an anti-solvent. The crystals appeared immediately. The crystals were filtered and dried at 40° C. The crystals were characterized as a mixture of fluazinam Form I and Form While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A process for preparing a pyridinamine compound represented by the structure of formula (I)

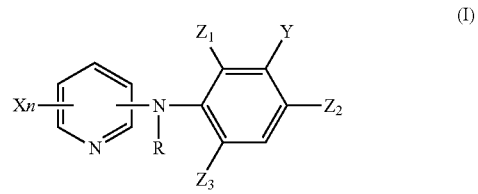

wherein
X is a trifluoromethyl group, a halogen atom, a $C_1$-$C_6$ alkyl group or a $C_1$-$C_6$ alkoxy group;
N is an integer of 0 to 4;
R is a hydrogen atom or an acetyl group;
Y is a hydrogen atom, a halogen atom, a $C_1$-$C_6$ alkoxy group, a $C_1$-$C_6$ thioalkyl group, a hydroxy group, an azido group, a phenoxy group or a phenoxy group in which the phenyl is substituted with a hydroxy;
and
$Z_1$, $Z_2$ and $Z_3$ are independently a trifluoromethyl group or a nitro group, the process comprising reacting a compound of formula (A)

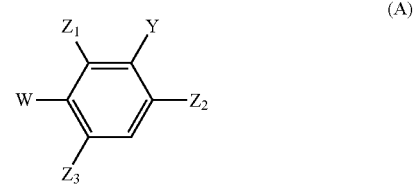

with a compound of formula (B)

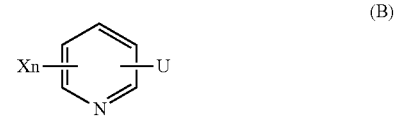

wherein X, Y, $Z_1$, $Z_2$, $Z_3$ and n in the formulas (A) and (B) are defined above; one of U and W is amino and the other is a leaving group selected from the group consisting of halogen, alkyl sulfonyl and arylsulfonyl in the presence of a base,
in a reaction solvent of methyl isobutyl ketone (MIBK).

2. The process according to claim 1, wherein the compound of formula (I) is 3-chloro-N-(3-chloro-5-trifluoromethyl-2-pyridyl)-α,α,α-trifluoro-2,6-dinitro-p-toluidine (fluazinam), represented by the structure of formula (3):

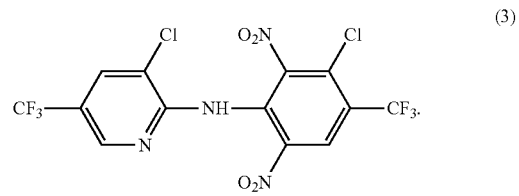 [SMILES: O=[N+]([O-])c1cc(C(F)(F)F)c(Cl)c([N+](=O)[O-])c1Nc1ncc(C(F)(F)F)cc1Cl]

3. The process according to claim 1, wherein the base is selected form the group consisting of alkali metal hydroxides, alkali metal carbonates, hydrides, alkaline earth metal hydroxides and alkaline earth metal carbonates.

4. The process according to claim 3, wherein the base is potassium hydroxide or sodium hydroxide.

5. The process according to claim 1, wherein the solvent is pure MIBK.

6. The process according to claim 1, wherein the solvent is a recycled azeotrope of MIBK containing about 1.6% water.

7. The process according to claim 1, further comprising the step of isolating the compound of formula (I) by adding an aqueous acid to form a mixture comprising an organic layer and an aqueous layer, and isolating the compound of formula (1) from the organic layer.

8. The process according to claim 1, further comprising the step of purifying the compound of formula (I) by crystallization from a solvent or mixture of solvents.

9. The process according to claim 8, wherein the crystallization solvent is ethanol.

10. The process according to claim 1, wherein the reagents to solvent ratio is greater than about 10% w/v.

11. A process according to claim 1, further comprising purifying the compound represented by the structure of formula (1)

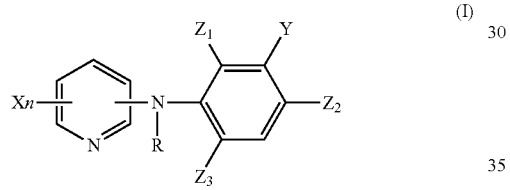

wherein
X is a trifluoromethyl group, a halogen atom, a $C_1$-$C_6$ alkyl group or a $C_1$-$C_6$ alkoxy group;
N is an integer of 0 to 4;
R is a hydrogen atom or an acetyl group;
Y is a hydrogen atom, a halogen atom, a $C_1$-$C_6$ alkoxy group, a $C_1$-$C_6$ thioalkyl group, a hydroxy group, an azido group, a phenoxy group or a phenoxy group in which the phenyl is substituted with a hydroxy; and
$Z_1$, $Z_2$ and $Z_3$ are independently a trifluoromethyl group or a nitro group;
by the step of crystallizing said compound from a solvent or a mixture of solvents.

12. The process according to claim 11, wherein the crystallization solvent is ethanol.

13. A process for preparing 3-chloro-N-(3-chloro-5-trifluoromethyl-2-pyridyl)-α,α,α-trifluoro-2,6-dinitro-p-toluidine (fluazinam) represented by the structure of formula (3):

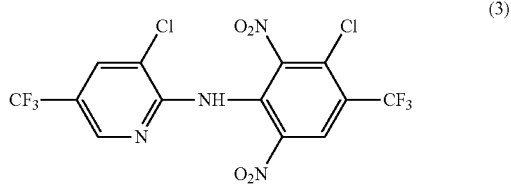 [SMILES: O=[N+]([O-])c1cc(C(F)(F)F)c(Cl)c([N+](=O)[O-])c1Nc1ncc(C(F)(F)F)cc1Cl]

the process comprising reacting a compound of formula (1)

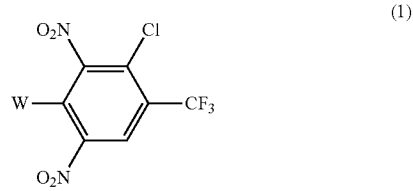

with a compound of formula (2)

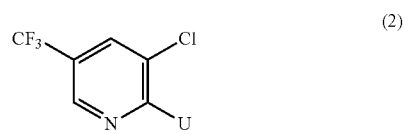

wherein one of U and W is amino and the other is a leaving group selected from the group consisting of halogen, alkylsulfonyl and arylsulfonyl in the presence of a base, in a reaction solvent of methyl isobutyl ketone (MIBK).

14. The process according to claim 13, wherein the compound of formula (1) is represented the structure of formula (1A), and the compound of formula (2) is represented by the structure of formula (2A):

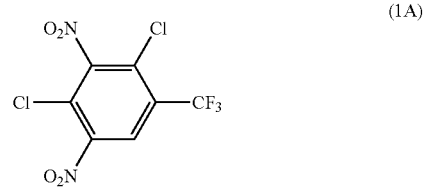 [SMILES: O=[N+]([O-])c1cc(C(F)(F)F)c(Cl)c([N+](=O)[O-])c1Cl]

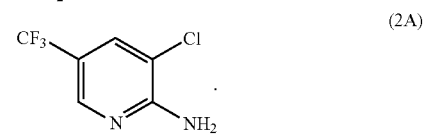

15. The process according to claim 14, wherein the base is selected form the group consisting of alkali metal hydroxides, alkali metal carbonates, hydrides, alkaline earth metal hydroxides and alkaline earth metal carbonates.

16. The process according to claim 15, wherein the base is potassium hydroxide or sodium hydroxide.

17. The process according to claim 13, wherein the solvent is pure MIRK.

18. The process according to claim 13, wherein the solvent is a recycled azeotrope of MIBK containing about 1.6% water.

19. The process according to claim 13, further comprising the step of isolating fluazinam by adding an aqueous acid to form a mixture comprising an organic layer and an aqueous layer, and isolating fluazinam from the organic layer.

20. The process according to claim 13, further providing a step of purifying fluazinam by crystallization from a solvent or mixture of solvents.

21. The process according to claim 20, wherein the crystallization solvent is ethanol.

22. The process according to claim 13, wherein the reagents to solvent ratio is greater than about 10% w/v.

23. The process of claim 13, further comprising purifying 3-chloro-N-(3-chloro-5-rifluoromethyl-2-pyridyl)-α,α,α-trifluoro-2,6-dinitro-p-toluidine (fluazinam) by the step of crystallizing said compound from a solvent or mixture of solvents.

24. The process according to claim 23, wherein the crystallization solvent is ethanol.

25. A process for preparing fluazinam represented by the structure of formula (3)

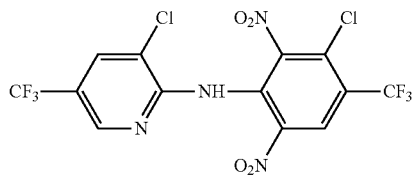
(3)

the process comprising reacting a compound of formula (1)

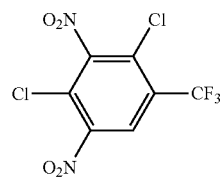
(1)

with a compound of formula (2)

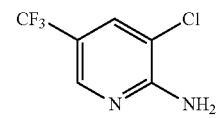
(2)

in the presence of a base,
in a reaction solvent of methyl isobutyl ketone (MIBK).

* * * * *